(12) United States Patent
Perrault et al.

(10) Patent No.: US 6,833,453 B2
(45) Date of Patent: Dec. 21, 2004

(54) METHODS OF PRODUCING OXAZOLIDINONE COMPOUNDS

(75) Inventors: William R. Perrault, Kalamazoo, MI (US); Robert C. Gadwood, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 203 days.

(21) Appl. No.: 09/982,157

(22) Filed: Oct. 17, 2001

(65) Prior Publication Data

US 2002/0086900 A1 Jul. 4, 2002

Related U.S. Application Data

(60) Provisional application No. 60/241,122, filed on Oct. 17, 2000.

(51) Int. Cl.$^7$ ............... C07D 263/04; C07D 413/02
(52) U.S. Cl. ............... 544/137; 544/369; 546/271.4; 548/229; 548/255; 548/262.2; 548/311.1; 548/565; 548/952; 549/426; 549/60; 549/483
(58) Field of Search ............... 544/137, 369; 546/271.4; 548/229, 255, 262.2, 311.1, 565, 952; 549/426

(56) References Cited

U.S. PATENT DOCUMENTS

| | | | |
|---|---|---|---|
| 3,654,298 A | 4/1972 | Douzon et al. | 260/307 |
| 4,150,029 A | 4/1979 | Dostert et al. | 260/307 |
| 4,250,318 A | 2/1981 | Dostert et al. | 548/229 |
| 4,340,606 A | 7/1982 | Fugitt et al. | 424/272 |
| 4,476,136 A | 10/1984 | Dostert et al. | 424/272 |
| 4,705,799 A | 11/1987 | Gregory | |
| 4,948,801 A | 8/1990 | Carlson et al. | 514/307 |
| 5,164,510 A | 11/1992 | Brickner | 548/231 |
| 5,182,403 A | 1/1993 | Brickner | 548/231 |
| 5,225,565 A | 7/1993 | Brickner | 548/229 |
| 5,231,188 A | 7/1993 | Brickner | 548/221 |
| 5,247,090 A | 9/1993 | Brickner | 546/89 |
| 5,332,754 A | 7/1994 | Nakai et al. | 514/376 |
| 5,880,118 A | 3/1999 | Barbachyn et al. | |
| 6,069,160 A | 5/2000 | Stolle et al. | |
| 6,107,519 A | 8/2000 | Pearlman | |
| 6,227,985 B1 | 8/2001 | Gadwood et al. | |
| 6,281,210 B1 | 8/2001 | Hester, Jr. | |

FOREIGN PATENT DOCUMENTS

| | | | | |
|---|---|---|---|---|
| DE | 19802239 A1 | 7/1999 | ......... | C07D/417/04 |
| EP | 0 127 902 | 12/1984 | | |
| EP | 0 738 720 | 10/1996 | | |
| WO | WO 93 01174 | 1/1993 | ......... | C07D/217/06 |
| WO | WO 93/09103 | 5/1993 | ......... | C07D/263/20 |
| WO | WO 93/23384 | 11/1993 | ......... | C07D/263/20 |
| WO | WO 95/07271 | 3/1995 | ......... | C07D/263/20 |
| WO | WO 96/13502 | 5/1996 | ......... | C07D/413/10 |
| WO | WO 96/15130 | 5/1996 | ....... | C07D/491/048 |
| WO | WO 97/10223 | 3/1997 | | |
| WO | WO 99/03764 | 1/1999 | ........... | B65G/47/00 |
| WO | WO 99/03846 | 1/1999 | | |
| WO | WO 99/24393 | 5/1999 | ......... | C07D/233/16 |
| WO | WO 99/40094 | 8/1999 | ......... | C07D/498/04 |
| WO | WO 00/09463 | 2/2000 | ........... | C07B/53/00 |
| WO | WO 00/32599 | 6/2000 | | |
| WO | WO 01/09107 | 2/2001 | | |
| WO | WO 01/42242 | 6/2001 | | |
| WO | WO 01/44212 | 6/2001 | | |
| WO | WO 01/58885 | 8/2001 | | |

OTHER PUBLICATIONS

Barbachyn et al., "Synthesis and Structure Activity Relationships of New Tropone–Substituted Oxazolidinone Antibacterial Agents," *Abstracts of Papers, 35th Interscience Conference on Antimicrobial Agents and Chemotherapy*, San Francisco, CA, Sep. 1995; American Society for Microbiology; Washington, DC, 1995, Abstract No. F206.

Barbachyn et al., "Identification of a Novel Oxzolidinone (U–100480) with Potent Antimycobacterial Activity," *J. Med. Chem.*,39, 680–685 (1996).

Brickner et al., "Synthesis of U–100592 and U–100766, Two New Oxazolidinone Antibacterial Agents in Clinical Trials for Treatment of Multiply Resistant Gram Positive Infections," *Abstracts of Papers, 35th Interscience Conference on Antimicrobial Agents and Chemotherapy*, San Francisco, CA, Sep., 1995; American Society for Microbiology: Washington, DC, 1995, Abstract No. F208.

Brickner et al., "Identification of New Oxazolidinone Antibacterial Agents with Potent In Vitro Antimycobacterial Activity," *Abstracts of the 35th Interscience Conference on Antimicrobial Agents and Chemotherapy*, San Francisco, CA, Sep., 1995; and American Society for Microbiology: Washington, DC, 1995, Abstract No. F227.

Brickner et al., "Syntheses and Antibacterial Activity of U–100592 and U–100766, Two Oxazolidinone Antibacterial Agents for the Potential Treatment of Multidrug–Resistant Gram–Positive Bacterial Infections," *J. Med. Chem.*, 39, 673–679 (1996).

Gregory et al., "Antibacterials. Synthesis and Structure–Activity Studies of 2–Aryl–2–oxooxazolidines. 2.The "B" Group," *J. Med. Chem.*, 32, 1673 1681 (1989).

(List continued on next page.)

*Primary Examiner*—Joseph K. McKane
*Assistant Examiner*—Golamm MM Shameem
(74) *Attorney, Agent, or Firm*—Pharmacia & Upjohn Company; Thomas A. Wooton

(57) ABSTRACT

Methods of synthesizing pharmacologically useful oxazolidinones are disclosed, and, in particular, a method of manufacturing a 5-(tert-butylcarbamoyl)-aminomethyl-oxazolidinone by condensing a carbamate with a tert-butylcarbamoyl protected derivative of glycidylamine or 3-amino-1-halopropanol.

26 Claims, No Drawings

OTHER PUBLICATIONS

Gregory et al., "Antibacterials. Synthesis and Structure–Acitivity Studies of 2–Aryl–2–oxooxazolidines. 2.The "A" Group," *J. Med. Chem.,* 33, 2569–2578 (1990).

Hutchinson et al., "Piperazinyl Oxazolidinones: Structure Activity Relationships of a New Class of Oxazolidinone Antibacterial Agents," *Abstracts of the 35th Interscience Conference on Antimicrobial Agents and Chemotherapy*, San Francisco, CA, Sep., 1995; Amercian Society for Microbiology: Washington, DC, 1995, Abstract No. F207.

Kitchin et al., "Synthesis and Structure–Activity Relationships of a Series of Penicillin–Derived HIV Proteinase Inhibitors: Heterocyclic Ring Systems Containing $P_1'$ and $P_2'$ Substituents," *J. Med Chem.,* 37, 3707–3716 (1994).

Manninen et al., "Multicyclic Fused–Ring Oxazolidinone Antibacterial Agents," *Abstracts of Papers, 206th National Meeting of the American Chemical Society*, Chicago, IL, Aug., 1993 American Chemical Society: Washington, DC, 1993,ORGN 089.

Schaus et. al., "Dynamic Kinetic Resolution of Epichlorohydrin via Enantioselective Catalytic Ring Opening with $TMSN_3$. Practical Synthesis of Aryl Oxazolidinone Antibacterial Agents," *Tetrahedron Letters*, 37, 7937–40 (1996).

Wang et al., "Chiral Synthesis of DUP 721, A New Antibacterial Agent," *Tetrahedron Letters*, 45, 1323–1326 (1989).

METHODS OF PRODUCING OXAZOLIDINONE COMPOUNDS

CROSS-REFERENCE TO RELATED APPLICATION

This application claims the benefit of provisional patent application Ser. No. 60/241,122, filed Oct. 17, 2000.

FIELD OF THE INVENTION

The present invention relates to a method of preparing pharmacologically active oxazolidinones and various intermediates used in the method. The oxazolidinone derivatives are useful as broad spectrum antimicrobial agents which are effective against a variety of human and veterinary pathogens.

BACKGROUND OF THE INVENTION

Compounds that contain the 5-acetamidomethyl-oxazolidinone moiety are well known to persons skilled in the art as pharmacologically useful antibacterial agents. For example, U.S. Pat. Nos. 5,164,510, 5,182,403, and 5,225,565 disclose antibacterial 5'-indolinyl-oxazolidinones, 3-(5'-indazolyl)-oxazolidinones, and 3-(fused-ring substituted) phenyl-oxazolidinones, respectively. Similarly, U.S. Pat. Nos. 5,231,188 and 5,247,090 disclose several tricyclic [6.5.5] and [6.6.5]-fused ring-oxazolidinones which are useful pharmaceutical agents. International Publication WO93/09103 discloses antibacterial mono- and di-halophenyl-oxazolidinones.

Persons skilled in the art use two primary methods to prepare the 5-acetamidomethyl-oxazolidinone moiety of these therapeutic agents. The first method involves condensation of an aromatic carbamate (Ar—HN—C(=O)—OR) or aromatic isocyanate (Ar—N=C=O) with a halopropanediol or another nitrogen-free three-carbon reagent to provide an intermediate oxazolidinone having a hydroxymethyl substituent at the C-5 position of the oxazolidinone. The hydroxyl group then is replaced by an acetamido group to give a pharmacologically active 5-acetamidomethyl-oxazolidinone.

Many variants of this two-step process have been developed, and examples are illustrated in U.S. Pat. Nos. 4,150,029, 4,250,318, 4,476,136, and 4,340,606, which disclose the synthesis of 5-hydroxymethyl-oxazolidinones from amines (Scheme A). The mixture of enantiomers produced by this process are Scheme A

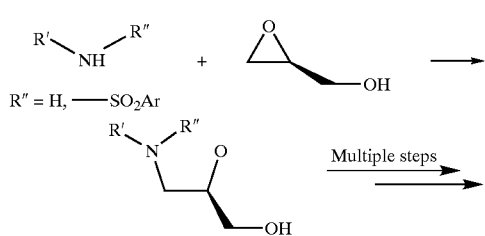

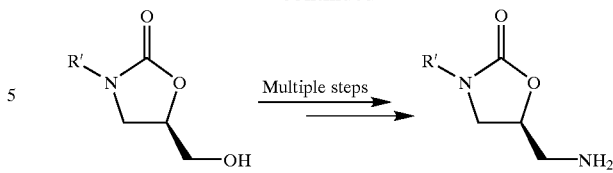

separated by fractional crystallization of their mandelic acid salts. The enantiomerically pure R-diol then is converted into the corresponding 5-(R)-hydroxymethyl-oxazolidinone by condensation with diethylcarbonate in the presence of sodium methoxide. The 5-(R)-hydroxymethyl-oxazolidinone then is aminated, and the resulting amine acylated in subsequent steps.

Likewise, U.S. Pat. No. 4,948,801, *J. Med. Chem.*, 32, 1673 (1989), and *Tetrahedron*, 45, 1323 (1989) disclose a method of producing oxazolidinones which comprises reacting an isocyanate (R—N=C=O) with (R)-glycidyl butyrate in the presence of a catalytic amount of a lithium bromide-tributylphosphine oxide complex at 135–145° C. to produce the corresponding 5-(R)-butyryloxymethyl-oxazolidinone. The butyrate ester then is hydrolyzed in a subsequent step to provide the corresponding 5-(R)-hydroxymethyl-oxazolidinone. The 5-(R)-hydroxymethyl-oxazolidinone then is aminated in a subsequent step.

Similarly, the following references disclose variations of the reaction of a carbamate with glycidyl butyrate: *Abstracts of Papers*, 206th National Meeting of the American Chemical Society, Chicago, Ill., August, 1993; American Chemical Society: Washington, D.C., 1993; ORGN 089; *J. Med. Chem.*, 39, 673 (1996); *J. Med. Chem.*, 39, 680 (1996); International Publications WO93/09103, WO93/23384, WO95/07271, WO96/13502, and WO96/15130; *Abstracts of Papers*, 35th Interscience Conference on Antimicrobial Agents and Chemotherapy, San Francisco, Calif., September, 1995; American Society for Microbiology: Washington, D.C., 1995, Abstract No. F208; *Abstracts of Papers*, 35th Interscience Conference on Antimicrobial Agents and Chemotherapy, San Francisco, Calif., September, 1995; American Society for Microbiology: Washington, D.C., 1995, Abstract No. F207; *Abstracts of Papers*, 35th Interscience Conference on Antimicrobial Agents and Chemotherapy, San Francisco, Calif., September, 1995; American Society for Microbiology: Washington, D.C., 1995, Abstract No. F206; *Abstracts of Papers*, 35th Interscience Conference on Antimicrobial Agents and Chemotherapy, San Francisco, Calif., September, 1995; and American Society for Microbiology: Washington, D.C., 1995, Abstract No. F227. The disclosed reactions use either n-butyllithium, lithium diusopropylamide, or lithium hexamethyldisilazide as the base to generate the nucleophilic anion or the carbamate over a temperature range of −78° C. to −40° C., followed by addition of the glycidyl butyrate at −78° C., and warming to 20–25° C. to produce the 5-(R)-hydroxymethyl-oxazolidinones wherein the ester is cleaved during the reaction.

As stated previously, the 5-(R)-hydroxymethyl-oxazolidinones then are aminated and acylated in subsequent steps. For example, International Publication WO95/07271 discloses the ammonolysis of 5-(R)-methylsulfonyloxymethyl-oxazolidinones. Likewise, U.S. Pat. No. 4,476,136 discloses a method of transforming 5-hydroxymethyl-oxazolidinones to the corresponding 5-(S)-aminomethyl-oxazolidinones (X) by treatment with methanesulfonyl chloride, followed by potassium phthalimide, then followed by hydrazine. *J. Med. Chem.*, 32, 1673 (1989) and *Tetrahedron*, 45, 1323 (1989) disclose a method of transforming 5-hydroxymethyl-oxazolidinones into the corresponding 5-(S)-acetamidomethyl-oxazolidinones by treating with methanesulfonyl chloride or tosyl chloride, followed by the stepwise addition of sodium azide, trimethylphosphite, or platinum dioxide/hydrogen, and acetic anhydride or acetyl chloride to give the desired 5-(S)-acetamidomethyl-oxazolidinone. Likewise, U.S. provisional application Serial No. 60/015,499 discloses a method of preparing 5-(S)-hydroxymethyl-oxazolidinone intermediates, as well as a process to convert these intermediates into 5-aminomethyl-oxazolidinone intermediates which can be acylated to produce pharmacologically active 5-(S)-acetamidomethyl-oxazolidinones. U.S. Pat. No. 3,654, 298 discloses the synthesis of 5-alkoxymethyl-3-aryl-oxazolidinones by sodium ethoxide induced cyclization of chlorocarbamates.

The second method (Scheme B) involves condensation of an aromatic carbamate (a) or isocyanate (b) with a protected nitrogen (NP)-containing three-carbon reagent to provide an oxazolidinone having the desired amine functionality at the 5-position (e). For example, *J. Med. Chem.*, 33, 2569 (1990)

Scheme B

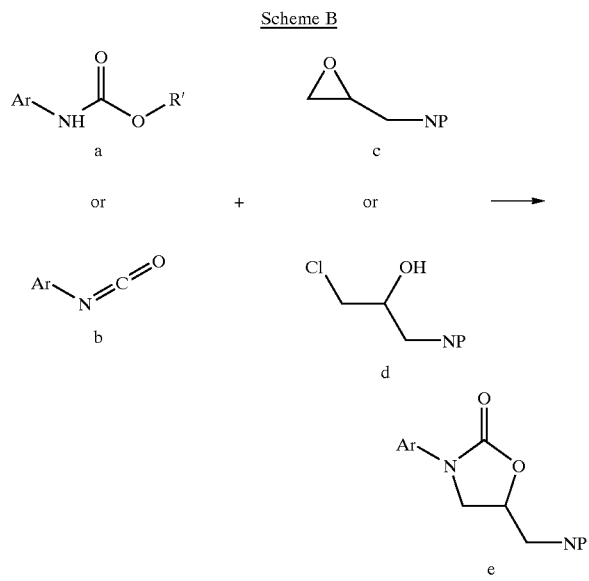

discloses the condensation of an isocyanate (b) with racemic glycidyl azide (c, NP=$N_3$) to provide a racemic 5-azidomethyl-oxazolidinone (e). Two subsequent steps are required to convert the racemic azidomethyl-oxazolidinone into a racemic 5-acetamidomethyl-oxazolidinone (e, NP=NHAc), which has antibiotic activity.

International Publication WO99/24393 discloses the reaction of a benzylcarbamoyl amine with three carbon reagents containing amines (NP=$NH_2$), acetamides (NP=NHAc), benzalimines (NP=N=C—Ph), or phthalimides. Likewise, *Tetrahedron Letters*, 37, 7937–40 (1996) discloses a synthesis of acetamidomethyl-oxazolidinones involving the process of condensing a carbamate with 1.1 equivalents of n-butyl lithium (tetrahydrofuran (THF), −78° C.), followed by 2 equivalents of S-glycidylacetamide (a, NP=—NHAc), to give the corresponding 5-(S)-acetamidomethyl-oxazolidinone (e). The S-glycidylacetamide can be made by the procedure disclosed in Jacobsen et. al., *Tet. Lett.* 37, 7937 (1996).

The S-enantiomer of epoxide (c) (Scheme B, NP=$NHCO_2$t-Bu) is well known in the literature, and has been used to prepare oxazolidinones as disclosed in International Publications WO 99/40094 and WO 99/3764, and German Patent application DE 19802239 A1, although by different routes than that shown in Scheme B. The (S)-epoxide (c) has been prepared by a hydrolytic kinetic resolution of the racemic epoxide as disclosed in WO 00/09463, and from R-glycidol as disclosed in WO 93/01174 and *J. Med. Chem.*, 37, 3707 (1994). However, the (S)-epoxide has not been prepared in crystalline form.

The prior art is silent with respect to the use of carbamates (a) or isocyanates (b) in condensations with tert-butylcarbamoyl-, (BOC), or other carbamoyl-protected nitrogen-containing three-carbon reagents (c,d, NP=NCOOR") to directly form oxazolidinones (e). The present invention involves condensation of a carbamate with a carbamoyl-protected derivative of glycidylamine or 3-amino-1-halo-2-propanol. The use of the carbamoyl protecting group, and specifically a tert-butylcarbamoyl (BOC) protecting group, results in a more facile reaction, with a greater yield, compared to the prior art. For example, the analogous acetamide reaction (Scheme B, NP=NHAc) typically requires the use of two equivalents of this reagent for the condensation to occur. In contrast, only 1.3 equivalents of the tert-butylcarbamoyl reagent (Scheme B, NP=NHBOC) is required to obtain comparable yields. The success of such a carbamate condensation is both surprising and unexpected because of the apparent steric hindrance of the tert-butylcarbamoyl group.

The present invention also is directed to the conversion of an isocyanate into the (S)-enantiomer of a 5-substituted-oxazolidinone in a single step. The (S)-enantiomers of 5-substituted-oxazolidinones have greater antibiotic activity than the racemates. U.S. Pat. No. 5,332,754 discloses that racemic 5-acetamidomethyl-oxazolidinones can be synthesized in one step by condensation of a carbamate with racemic glycidyl acetamide in the presence of a base, such as an amine, alkali metal hydroxide, an alkali metal alkoxide, and the like, and that it is preferred to carry out the reaction at an elevated temperature, preferably at a temperature between 90° C. and 110° C. The patent provides no yields or description of this process in the examples, and evidence indicates that, under these conditions, rearrangement to an undesired side product occurs. Indeed, the examples do not disclose a one-step process, but disclose multi-step routes that are known to those skilled in the art, including mesylation of a 5-hydroxymethyl-oxazolidinone followed by azide displacement, hydrogenation, and acetylation of the amine.

The present method differs in that a) the reaction is between a protected carbamate (I) and an (S)-glydidyl alkylcarbamate (II), an (S)-chlorohydrin alkylcarbamate (IV), or an (S)-chloroacetate alkylcarbamate (V) (Scheme B, NP=NHalkyl); b) the reaction is between an isocyanate (VI) and an (S)-glydidyl alkylcarbamate (II), an (S)-chlorohydrin alkylcarbamate (IV), or an (S)-chloroacetate alkylcarbamate (V) (Scheme B, NP=NHalkyl), and c) the reaction is performed under conditions such that competing rearrangement to the undesired side products is largely suppressed.

SUMMARY OF THE INVENTION

The present invention is directed to a method of synthesizing oxazolidinones and intermediate compounds used in the synthesis. As shown in Schemes 1, 2, and 3 below, one aspect of the present invention is to provide an Scheme 1

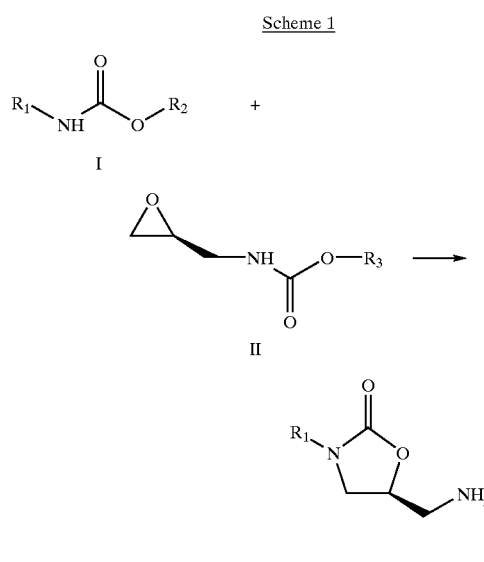

Scheme 2

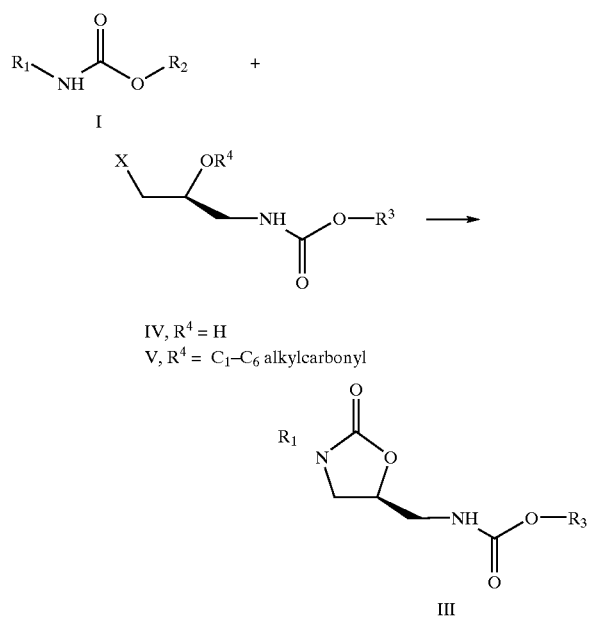

Scheme 3

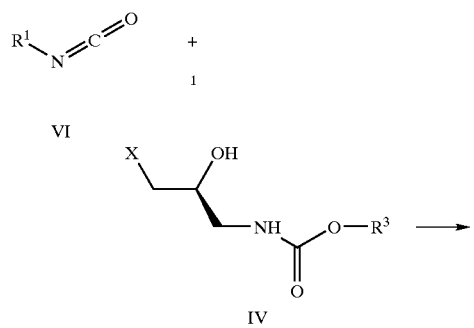

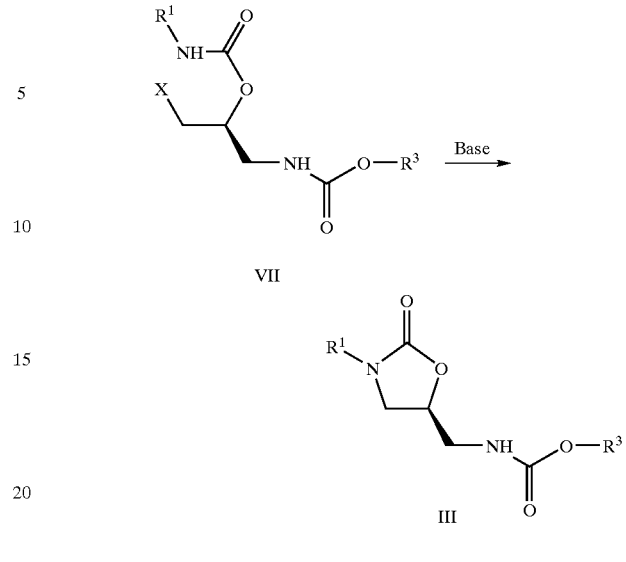

S)-oxazolidinone alkylcarbamoyl intermediate of structural formula (III), an (S)-secondary alcohol of structural formula (IV), and an (S)-ester/protected alcohol of structural formula (V), or a salt or hydrate thereof or acceptable salts, hydrates, or pro-compounds thereof, wherein $R^1$ is optionally substituted aryl; $R^2$ is selected from the group consisting of $C_1$–$C_{20}$ alkyl, $C_3$–$C_7$ cycloalkyl, aryl optionally substituted with one or two $C_1$–$C_3$ alkyl or halogen groups, allyl, 3-methylallyl, 3,3-dimethylallyl, vinyl, styrylmethyl, benzyl optionally substituted on the aryl with one or two Cl, $C_1$–$C_4$ alkyl, nitro, cyano, or trifluoromethyl groups, 9-fluorenylmethyl, trichloromethylmethyl, 2-trimethylsilylethyl, phenylethyl, 1-adamantyl, diphenylmethyl, 1,1-dimethylpropargyl, 2-furanylmethyl, isobornyl, and hydrogen; $R^3$ is $C_1$–$C_{10}$ alkyl; $R^4$ is H or $C_1$–$C_5$ alkylcarbonyl; and X is halogen, alkylsulfonyloxy, or arylsulfonyloxy.

Another aspect of the present invention is to provide an (S)-epoxide of structural formula (II), an (S)-oxazolidinone t-butylcarbamoyl intermediate of structural formula (III), an (S)-secondary alcohol of structural formula (IV), and an (S)-ester/protected alcohol of structural formula (V), or acceptable salts, hydrates, or pro-compounds thereof, in crystalline form, and a process of preparing these compounds in crystalline form.

One other aspect of the present invention, as shown in Scheme 4, is to

Scheme 4

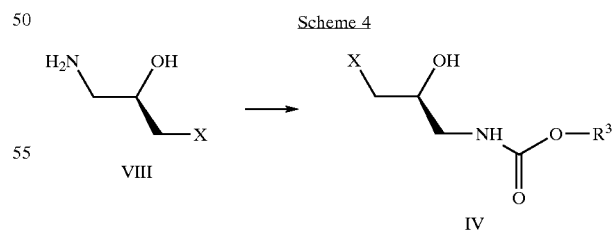

provide a process for the preparation of an (S)-3-carbon carbamoyl alcohol of the structural formula (IV) which comprises (a) contacting a dialkyldicarbonate with an (S)-amino alcohol of formula (VIII) in the presence of a base, such as a tri(alkyl)amine. The (S)-3-carbon carbamoyl alcohol can be isolated in crystalline form after recrystallization.

Yet another aspect of the present invention, as shown in Scheme 5,

Scheme 5

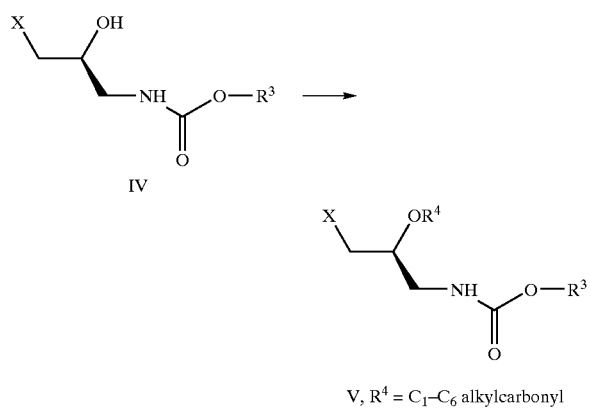

V, $R^4$ = $C_1$–$C_6$ alkylcarbonyl is to provide a process for preparing a se cond ary protected-alcohol of structural formula (V) which comprises contacting an (S)-3-carbon amino alcohol of structural formula (IV) with an acylating agent and a base, such as a tri(alkyl)amine. The (S)-secondary protected-alcohol can be isolated in crystalline form after recrystallization.

Yet another aspect of the present invention, as shown in Scheme 6,

Scheme 6

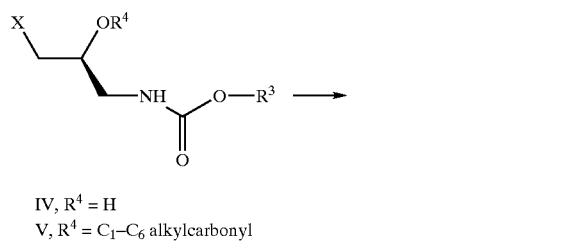

IV, $R^4$ = H
V, $R^4$ = $C_1$–$C_6$ alkylcarbonyl

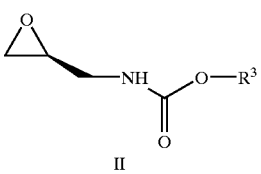

is to provide a process for the preparation of a (S)-epoxide of structural formula (II) which comprises contacting an (S)-3-carbon amino alcohol of structural formula (IV) or (S)-secondary protected-alcohol of structural formula (V) with a base. The (S)-epoxide can be isolated in crystalline form after chromatography.

Another aspect of the present invention is to provide a process for the production of an (S)-oxazolidinone of structural formula (III) which comprises contacting a carbamate of structural formula (I) with an oxygenated amino reagent selected from the group consisting of an (S)-t-butylcarbamyl secondary alcohol of structural formula (IV), an (S)-t-butylcarbamyl epoxide of structural formula (II), or an (S)-t-butylcarbamyl ester of structural formula (V), in the presence of a lithium cation and a base whose conjugate acid has a pKa greater than about 8.

An additional aspect of the present invention, as shown in Scheme 7, is

Scheme 7

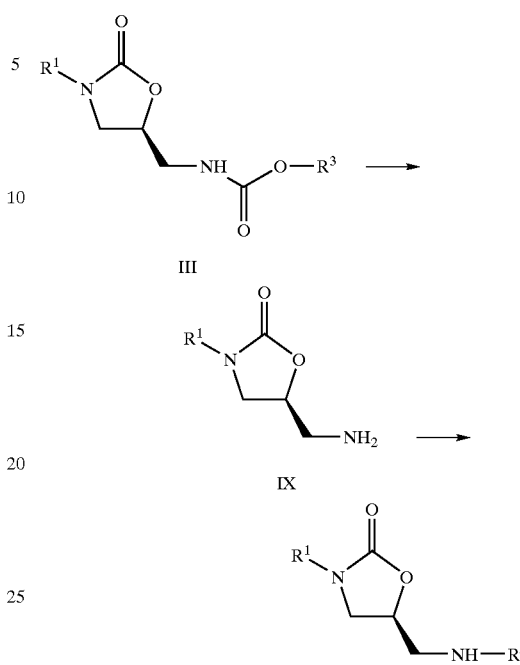

X, $R^5$ = $C_1$–$C_6$ alkylcarbonyl or $C_1$–$C_6$ cycloalkylcarbonyl
XI, $R^5$ = $C_1$–$C_6$ alkylthiocarbonyl or $C_1$–$C_6$ cycloalkylthiocarbonyl to provide a process for the production of an (S)-3,5-disubstituted-oxazolidinone of the structural formula (X) and (XI) which comprises (a) contacting a carbamate of structural formula (I) with an (S)-protected alcohol of formula (V) in the presence of a lithium cation and a base whose conjugate acid has a pKa of greater than about 8 to provide an (S)-protected-oxazolidinone of the structural formula (III) (see Scheme 2), (b) contacting the reaction product of step (a) with aqueous acid to produce an (S)-oxazolidinone free amine of structural formula (IX), and (c) contacting the product of step (b) with a base, such as a tri($C_1$–$C_5$ alkyl)amine, and an acylating or thioacylating agent selected from the group consisting of (i) an acid anhydride of the structural formula O($R^5$)$_2$, (ii) an activated acid of the structural formula $R^5$X to provide (X) or (iii) a dithioester of the structural formula $R^5$S(C=S)$R^5$ to provide (XI), wherein $R^5$ is $C_1$–$C_6$ alkylcarbonyl, $C_1$–$C_6$ cycloalkylcarbonyl, $C_1$–$C_6$ alkylthiocarbonyl, or $C_1$–$C_6$ cycloalkylthiocarbonyl, and X is halogen, alkylsulfonyloxy, or arylsulfonyloxy.

A further aspect of the present invention is to provide a one pot process for the production of an (S)-oxazolidinone of structural formula (X) and (XI) which comprises (a) contacting a carbamate of formula (I) with either an (S)-t-butylcarbamyl secondary alcohol of the structural formula (IV) or an (S)-t-butylcarbamyl epoxide of the structural formula (II), in the presence of a lithium cation and a base whose conjugate acid has a pKa of greater than about 8, (b) contacting the product of step (a) with aqueous acid, and (c) contacting the reaction product of step (b) with a base, such as a tri($C_1$–$C_5$ alkyl)amine, and and an acylating or thioacylating agent selected from the group consisting of (i) an acid anhydride of the structural formula O($R^5$)$_2$, (ii) an activated acid of the structural formula $R^5$X, or (iii) a dithioester of the structural formula $R^5$S(C=S)$R^5$, wherein $R^5$ is $C_1$–$C_6$ alkylcarbonyl, $C_1$–$C_6$ cycloalkylcarbonyl, $C_1$–$C_6$ alkylthiocarbonyl, or $C_1$–$C_6$ cycloalkylthiocarbonyl, and X is halogen, alkylsulfonyloxy, or arylsulfonyloxy.

DETAILED DESCRIPTION OF THE PREFERRED EMBODIMENTS

As used herein, the terms and phrases have the meanings, definitions, and explanations known in the art. Some of the more commonly used phrases are described in more detail below.

"Alkyl" refers to a cyclic, branched, or straight chain aliphatic group containing only carbon and hydrogen, for example, methyl, pentyl, and adamantyl. Alkyl groups can be unsubstituted or substituted with one or more substituents, e.g., halogen, alkoxy, acyloxy, amino, hydroxyl, mercapto, carboxy, benzyloxy, aryl, and benzyl. Alkyl groups can be saturated or unsaturated (e.g., containing alkenyl or alkynyl subunits at one or several positions). Typically, alkyl groups contain 1 to about 12 carbon atoms, preferably 1 to about 10, or 1 to about 8 carbon atoms.

"Aryl" refers to a monovalent aromatic carbocyclic group having a single ring (e.g., phenyl), multiple rings (e.g., biphenyl), or multiple condensed rings (e.g., naphthyl or anthryl). Aryl groups can be unsubstituted or substituted with amino, hydroxyl, alkyl, heteroalkyl, alkoxy, halo, mercapto, sulfonyl, nitro, and other substituents. Typically, the aryl group is a substituted single ring compound. For example, the aryl group is a substituted phenyl ring.

The term "halo" or "halogen" is defined herein to include fluorine, bromine, chlorine, and iodine.

The term "alkoxy" and "aryloxy" are defined as —OR, wherein R is alkyl or aryl, respectively.

The term "hydroxy" is defined as —OH.

The term "amino" is defined as —$NR_2$, wherein each R, independently, is alkyl or hydrogen.

The term "alkylcarbonyl" is defined as R—C(=O)—, where R is alkyl.

The term "alkylthiocarbonyl" is defined as R—C(=S)—, where R is alkyl.

The term "alkylsulfonyloxy" is defined as R—$SO_3$—, where R is alkyl.

The term "arylsulfonyloxy" is defined as R—$SO_3$—, where R is aryl.

The oxazolidinone ring system is numbered as follows:

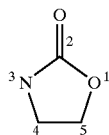

The present invention is directed both to novel synthetic intermediates and to methods of preparing pharmaceutically active and commercially valuable oxazolidinone antibiotics, as defined below by the following general synthetic schemes.

Scheme 1

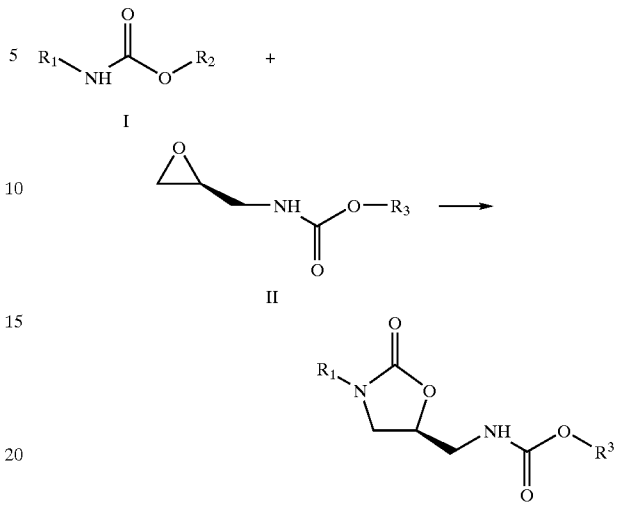

Scheme 1 sets forth the reaction between a carbamate (1) and an (S)-epoxide (II) to produce the corresponding (S)-oxazolidinone (III). Carbamates (I) are known to those skilled in the art, or can be readily prepared from known compounds by methods known to those skilled in the art (See example 1). Suitably, $R^1$ is an aryl group, optionally substituted. Preferably, $R^1$ is:

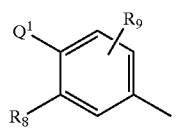

wherein $Q^1$ is: $R^{10}R^{11}N$,

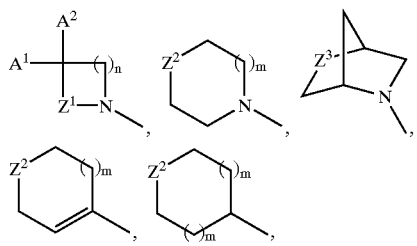

or $Q^1$ and $R^8$ taken together are dihydropyrrolidine, optionally substituted with $R^{12}$;

$Z^1$ is $CH_2(CH_2)_p$, $CH(OH)(CH_2)_p$, or C(O);
$Z^2$ is(O)S, O, or $N(R^{13})$;
$Z^3$ is $(O)_pS$ or O;
$A^1$ is H or $CH_3$;
$A^2$ is selected from the group consisting of:
    a) H,
    b) HO,
    c) $CH_3$,
    d) $CH_3O$,
    e) $R^4OCH_2$=C(O)NH,
    f) $R^5OC(O)NH$,
    g) ($C_1$–$C_3$)alkoxycarbonyl,
    h) $HOCH_2$,
    i) $CH_3ONH$,
    j) $CH_3C(O)$, k) $CH_3C(O)CH_2$,
l) $CH_3C(OCH_2CH_2O)$, and
m) $CH_3C(OCH_2CH_2O)CH_2$,
or $A^1$—C—$A^2$ taken together are $CH_3$—$C(OCH_2CH_2O)$, $C(O)$, or $C(=NR^{22})$;

$R^8$ is H or F, or is taken together with $Q^1$ as above;

$R^9$ is H or F;

$R^{10}$ and $R^{11}$ are taken together with the N atom to form a 3,7-diazabicyclo[3.3.0]octane, pyrrole, pyrazole, imidazole, 1,2,3-triazole, 1,2,4-triazole, morpholine or a piperazine group, optionally substituted with $R^{13}$;

$R^{12}$ is selected from the group consisting of:
 a) $CH_3C(O)$—,
 b) $HC(O)$—,
 c) $Cl_2CHC(O)$—,
 d) $HOCH_2C(O)$—,
 e) $CH_3SO_2$—,
 f) $F_2CHC(O)$—,
 g) $H_3CC(O)OCH_2C(O)$—,
 h) $HC(O)OCH_2C(O)$—,
 i) $R^{21}C(O)OCH_2C(O)$—,
 j) $H_3CCHCH_2OCH_2C(O)$—,
 k) benzyl $OCH_2C(O)$—,
 l)–m)

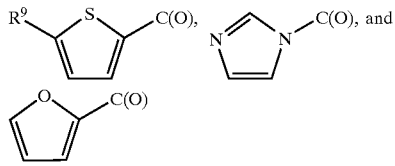

$R^{13}$ is selected from the group consisting of:
 a) $R^{14}OC(^{16})(R^{17})C(O)$—,
 b) $R^{15}OC(O)$—,
 c) $R^8C(O)$—,
 d) $H_3CC(O)(CH_2)_2C(O)$—,
 e) $R^{19}SO_2$—,
 f) $HOCH_2C(O)$—,
 g) $R^{20}(CH_2)_2$—,
 h) $R^{21}C(O)OCH_2C(O)$—,
 i) $(CH_3)_2NCH_2C(O)NH$—,
 j) $NCCH_2$—,
 k) $F_2CHCH_2$—,
 l)–m)

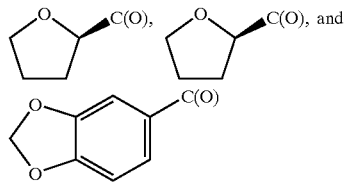

$R^{14}$ is H, $CH_3$, benzyl, or $CH_3C(O)$—;

$R^{15}$ is ($C_1$–$C_3$)alkyl, aryl, or benzyl;

$R^{16}$ and $R^{17}$, independently, are H or $CH_3$;

$R^{18}$ is selected from the group consisting of:
 a) H—,
 b) ($C_1$–$C_4$)alkyl,
 c) aryl($CH_2)_m$,
 d) $ClH_2C$—,
 e) $Cl_2HC$—,
 f) $FH_2C$—, g) $F_2HC$—, and
h) ($C_3$–$C_6$)cycloalkyl;

$R^{19}$ is selected from the group consisting of:
 a) $CH_3$,
 b) $CH_2Cl$,
 c) $CH_2CH=CH_2$,
 d) aryl, and
 e) $CH_2CN$;

$R^{20}$ is OH, $CH_3O$—, or F;

$R^{21}$ is:
 a) $CH_3$—,
 b) $HOCH_2$—,
 c) aniline, or
 d) $(CH_3)_2N-CH_2$—, $R^{22}$ is selected from the group consisting of:
 a) HO—
 b) $CH_3O$
 c) $H_2N$—
 d) $CH_3OC(O)O$—,
 e) $CH_3C(O)OCH_2C(O)O$—,
 f) aryl-$CH_2OCH_2C(O)O$—,
 g) $HO(CH_2)_2O$,
 h) $CH_3OCH_2O(CH_2)_2O$—, and
 i) $CH_3OCH_2O$—;

m is 0 or 1;

n is 1–3;

p is 0–2; and aryl is unsubstituted phenyl or phenyl unsubstituted with one of the following:
 a) F,
 b) Cl,
 c) $OCH_3$,
 d) OH,
 e) $NH_2$,
 f) ($C_1$–$C_4$)alkyl,
 g) $OC(O)OCH_3$, or
 h) $NO_2$;
and protected forms thereof.

Specific substituted $Q^1$ groups include, but are not limited to, 4-(benzyloxycarbonyl)-1-piperazinyl, 4-morpholinyl, and 4-hydroxyacetylpiperazinyl. Especially preferred $R^1$ groups include 3-fluoro-4-[4-(benzyloxycarbonyl)-1-piperazinyl]phenyl, 3-fluoro-4-(4-morpholinyl)phenyl, 4-(1,1-dioxohexahydro-1$\lambda^6$-thiopyran-4-yl)-3-fluorophenyl, 3-fluoro-4-tetrahydro-2H-thiopyran-4-ylphenyl, 3,5-difluoro-4-(4-thiomorpholinyl)phenyl, 3-fluoro-4-(3-thietanyl)phenyl, and 4-(1,1-dioxido-3-thietanyl)-3-fluorophenyl.

$R^2$ is selected from the group consisting of $C_1$–$C_{20}$ alkyl, $C_3$–$C_7$ cycloalkyl, aryl optionally substituted with one or two $C_1$–$C_3$alkyl or halogen groups, allyl, 3-methylallyl, 3,3-dimethylallyl, vinyl, styrylmethyl, benzyl optionally substituted on the phenyl with one or two Cl, $C_1$–$C_4$ alkyl, nitro, cyano, or trifluoromethyl groups, 9-fluorenylmethyl, trichloromethylmethyl, 2-trimethylsilylethyl, phenylethyl, 1-adamantyl, diphenylmethyl, 1,1-dimethylpropargyl, 2-fuiranylmethyl, isobornyl, and hydrogen. Preferably, $R^2$ is methyl. $R^3$ is $C_1$–$C_{10}$ alkyl, and, preferably, $R^3$ is $C_4$–$C_7$ tertiary alkyl.

The carbamate (I) and S-epoxide (II) are reacted in the presence of a base and a solvent. The identity of the base is not critical as long as the base is capable of deprotonating carbamate (I), i.e., a base whose conjugate acid has a pKa of greater than about 8. A preferred base is selected from the group consisting of an alkoxy group having one through seven carbon atoms; a carbonate; a methyl, sec-butyl or t-butyl carbanion; tri(alkyl)amine, wherein the alkyl group contains 1 through 5 carbon atoms; a conjugate base of carbamate (II); 1,8-diazabicyclo[5.4.0]undec-7-ene (DBU); 1,5-diazabicyclo[4.3.0]non-5-ene (DBN); N-methylpiperidine; N-methylmorpholine; and, 2,2,2-trichloroethoxide. The most preferred base is an alkoxy group having four or five carbon atoms, particularly t-amylate or t-butoxide. Sodium or potassium bases in combination with a lithium salt (such as, lithium chloride or lithium bromide) can be used to form the lithium cation and base in situ.

The identity of the solvent also is not critical, and includes, for example, cyclic ethers such as tetrahydrofuran (THF), amides such as dimethylformamide (DMF) and dimethylacetamide (DMAC), amines such as triethylamine, acetonitrile, and alcohols such as t-amyl alcohol and t-butyl alcohol. The choice of solvent is related to the solubility of carbamate (I) and the S-epoxide (II), and can be determined easily by those skilled in the art.

Another embodiment of the present invention is set forth in Scheme 2,

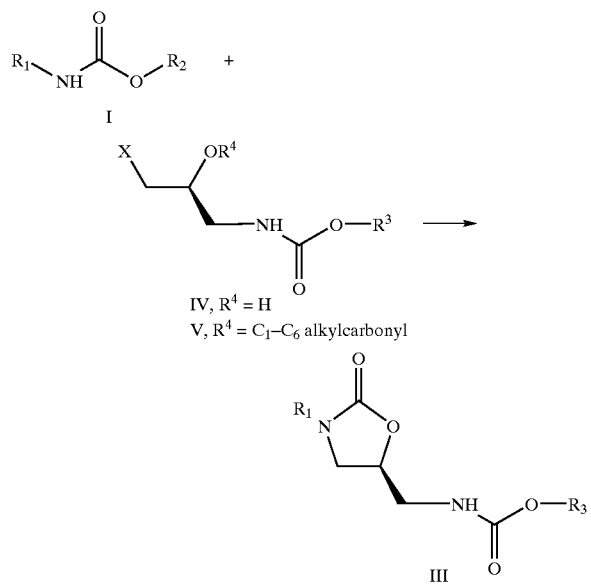

i.e., the reaction between a carbamate (I) with either an (5)-secondary alcohol (IV) or an (S)-ester (V) to provide a corresponding (S)-oxazolidinone (III). This process is performed in the same manner as that previously disclosed for Scheme 1.

A third process to produce the (S)-oxazolidinone (III) is set forth in Scheme 3 and involves a reaction between an isocyanate (VI) with either a (S)-secondary alcohol (IV) to give an (S)-intermediate (Ini) via compound (VII). This process is performed in a similar manner as that previously disclosed for Schemes 1 and 2.

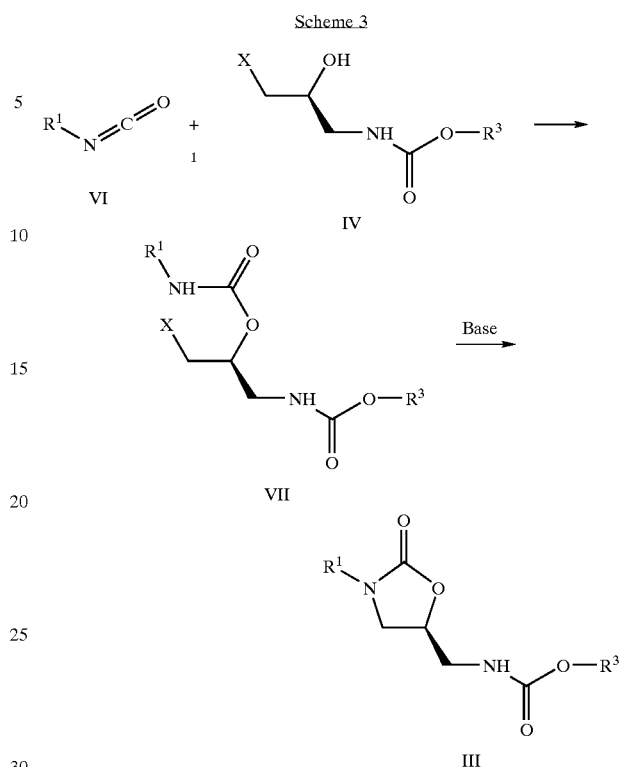

The three carbon nitrogen containing fragments, i.e., (S)-secondary alcohol (IV), (S)-epoxide (II), and (S)-ester (V), can be produced by1 different routes, as illustrated in Schemes 4, 5, and 6. Scheme 4 illustrates a process of preparing a

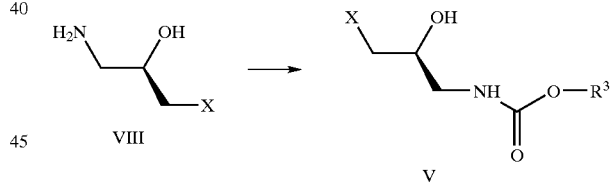

(S)-3-carbon amino alcohol (IV) from an (S)-amino alcohol (VIII) and a dialkyldicarbonate. For the (S)-amino alcohol (VIII), X can be halogen, alkylsulfonyloxy, or arylsulfonyloxy. A preferred X is Cl. The (S)-amino alcohols (VIII) are known to those skilled in the art or can readily be prepared from known compounds by methods disclosed in WO 99/24393 from commercially available S-epichlorohydrin. The (S)-amino alcohol can be isolated in crystalline form after recrystallization. The reaction of dialkyldicarbonate and the (S)-amino alcohol (VIII) is performed as set forth in Example 3.

It should be noted that starting with an enantiomerically pure (S)-amino alcohol (VIII) ultimately yields an enantiomerically pure (S)-protected alcohol (IV), (S)-ester (V), and (S)-epoxide (II). The absolute configuration of the carbon atom in the pharmacologically useful (S)-oxazolidinone compounds (X) and (XI) is "S", and therefore it is preferable to use enantiomerically pure (S)-amino alcohol (VIII) and obtain enantiomerically pure (S)-protected alcohol (IV), see Scheme 4. In the Schemes and the claims, the supra scripted "-(S)-" as -C-$^{(S)}$- denotes the asymmetric carbon atom has the appropriate enantiomeric configuration (S)- such that when this carbon atom becomes part of an (S)-oxazolidinone (III, X, or XI), it is the preferred enantiomer. If any of the chemical sequences of the processes of the present invention begins with an optically impure (racemic) form, rather than an enantiomerically pure form, the products obtained are the corresponding optically impure (racemic) forms.

Scheme 5 illustrates a process for converting an (S)-carbamoyl alcohol

Scheme 5

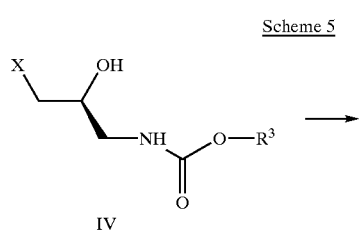

IV

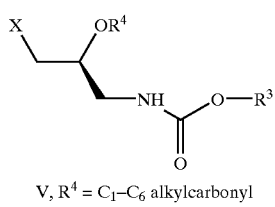

V, $R^4 = C_1-C_6$ alkylcarbonyl (IV) to a corresponding (S)-secondary ester protected alcohol (V). To convert an (S)-carbamoyl alcohol (IV) to a corresponding (S)-secondary ester/protected alcohol (V), the (S)-carbamoyl alcohol (IV) is reacted with an appropriate acylating reagent, such as an acyl halide or acyl anhydride, under acylation reaction conditions well known to those skilled in the art. The (S)-secondary protected-alcohol can be isolated in crystalline form after recrystallization. For example, an (S)-carbamoyl alcohol (IV) can be transformed to a corresponding (S)-secondary ester/protected alcohol (V) by reaction with acetic anhydride in triethylamine, as is set forth in Example 4. For the (S)-3-carbon amino alcohol (IV), X can be halogen, alkylsulfonyloxy, or arylsulfonyloxy, and preferably is Cl. For the corresponding corresponding (S)-secondary ester/protected alcohol (V), $R^4$ is $C_1-C_5$ alkylcarbonyl and preferably is acetyl. It is preferred that the acylating reagent be selected from the group consisting of an acid anhydride of the formula $O(R^5)_2$, wherein $R^5$ is $C_1-C_6$ alkylcarbonyl, or an activated acid of the formula $R^5$ X, wherein X can be halogen, alkylsulfonyloxy or arylsulfonyloxy and preferably is —Cl or —Br, and used in conjunction with base, preferably a tri($C_1-C_5$ alkyl)amine. It is more preferred that $R^5$ is acetyl and X is —Cl. Specifically, the more preferred acylating reagent is an acyl anhydride, and it is most preferred that the acyl anhydride is acetic anhydride.

Scheme 6 shows a process of preparing a (S)-epoxide (II) from either

Scheme 6

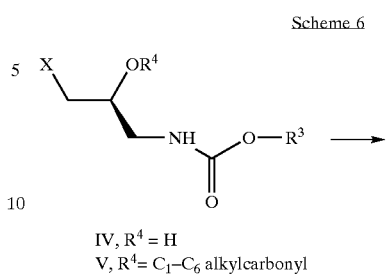

IV, $R^4 = H$
V, $R^4 = C_1-C_6$ alkylcarbonyl

II an (S)-3-carbon amino alcohol (IV) or an (S)-secondary ester/protected alcohol (V). The (S)-epoxide (II) can be obtained by reaction of an (S)-secondary ester/protected alcohol (V) with a base, such as potassium or lithium t-butoxide, in a solvent, such as methanol. The (S)-epoxide can be isolated in crystalline form after chromatography. An (S)-epoxide (II) can be produced from a corresponding (S)-secondary alcohol (IV) by reaction with lithium t-butoxide in methanol at 20° C., as is set forth in Example 5. For an (S)-secondary alcohol (IV) or (S)-secondary ester/ protected alcohol (V), it is preferred that $R^4$ is acetyl. For either an (S)-3-carbon amino alcohol (IV) or (S)-secondary ester/protected alcohol (V), X can be halogen, alkylsulfonyloxy, or arylsulfonyloxy, and preferably is Cl.

An (S)-oxazolidinone intermediate (III) is readily transformed to the corresponding pharmacologically active (S)-oxazolidinones (X) and (XI), as shown in Scheme 7. (S)-Oxazolidinone intermediate (III) first can be transformed to the Scheme 7

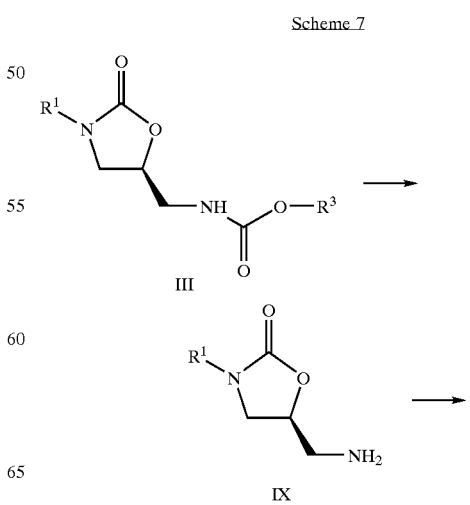

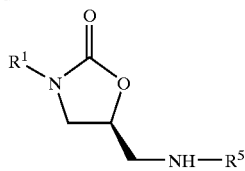

X, $R^5$ = $C_1$–$C_6$ alkylcarbonyl or $C_1$–$C_6$ cycloalkylcarbonyl
XI, $R^5$ = $C_1$–$C_6$ alkylthiocarbonyl or $C_1$–$C_6$ cycloalkylthiocarbonyl (S)-oxazolidinone free amine (IX). (S)-oxazolidinone free amine (IX) then is acylated with an appropriate acylating or thioacylating reagent, such as an activated acid, acyl halide, acyl anhydride, or dithioester, under acylation or thioacylation reaction conditions well known to those skilled in the art (see Examples 14 and 16, and WO 00/32599), to produce an (S)-oxazolidinone (X) or (XI) product, respectively.

Alternatively, the transformation from compound (III) to compound (X) or (XI) can be accomplished as a one pot process without isolating amine (IX). It is preferred that the acylating or thioacylating agent is selected from the group consisting of an acid anhydride of the structural formula $O(R^5)_2$, an activated acid of the structural formula $R^5X$, and a dithioester of the structural formula $R^5S(C=S)R^5$, wherein $R^5$ is $C_1$–$C_6$ alkylcarbonyl, $C_1$–$C_6$ cycloalkylcarbonyl, $C_1$–$C_6$ alkylthio-carbonyl, or $C_1$–$C_6$, cycloalkylthiocarbonyl, and X is halogen, alkylsulfonyloxy, or arylsulfonyloxy. It is preferred that the acylating agent or thioacylating agent is used in conjunction with a base, such as a tri($C_1$–$C_5$ alkyl)amine. It is more preferred that $R^5$ is acetyl and X is Cl. Specifically, it is more preferred that the acylating reagent is an acyl anhydride, and most preferably the acyl anhydride is acetic anhydride.

General Methods and Definitions

Reagents were obtained from commercial sources and used without further purification. All temperatures are in degrees Centigrade. When solvent pairs are used, the ratios of solvents used are volume/volume (v/v). When the solubility of a solid in a solvent is used the ratio of the solid to the solvent is weight/volume (wt/v). Reactions with moisture sensitive reagents were performed under a nitrogen atmosphere. Concentration of volumes was performed by reduced pressure rotary evaporation. Brine refers to an aqueous saturated sodium chloride solution. Chromatography (column and flash) refers to purification/separation of compounds expressed as (support/eluent). It is understood that the appropriate fractions are pooled and concentrated to give the desired compound(s). High performance liquid chromatography (HPLC) analysis was performed using a Dionex DX-500 system with UV detection at 229 NM. Thin layer chromatography (TLC) was performed using 250 micron Analtech silica GF plates. CMR refers to C-13 magnetic resonance spectroscopy, chemical shifts are reported in ppm downfield from tetramethylsilane (TMS). NMR refers to nuclear magnetic resonance spectroscopy. $^1$H NMR refers to proton nuclear magnetic resonance spectroscopy with chemical shifts reported in ppm downfield from TMS. $[I]^{22}D$ refers to the angle of plane polarized light (specific optical rotation) at 25° C. with the sodium D line (589 A). Mass spectromotry (MS) is expressed as m/e, m/z or mass/charge unit and is obtained using electron impact (EI), chemical ionization (CI) or fast atom bombardment (FAB) techniques. [M+H]$^+$ refers to the positive ion of a parent plus a hydrogen atom. Retention time (RT) is in minutes and refers to the elution time of the compound after injection. IR refers to infrared spectroscopy. FTIR refers to Fourier Transform IR.

EXAMPLES

The following detailed examples describe how to prepare the various compounds and/or perform the various processes of the invention, and are to be construed as merely illustrative, and not limitations of the preceding disclosure in any way whatsoever. Those skilled in the art will recognize appropriate variations from the procedures both as to reactants and as to reaction conditions and techniques.

Example 1

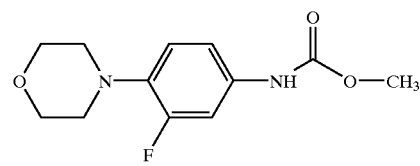

Preparation of N-Carbomethoxy-3-fluoro-4-morpholinylaniline (Compound I, $R^1$=3-Fluoro-4-morpholinylphenyl)

Step A: 3-Fluoro-4-morpholinylaniline 3,4-Difluoronitrobenzene (25.196 g, 158.38 mmol) was added to a mixture of morpholine (60.0 ml, 688 mmol, 4.34 eq) in THF (30 ml) at 14° C. The mixture was permitted to warm to 10° C., then maintained at 10–13° C. for 1 hr. A mixture of citric acid monohydrate (75 g, 357 mmol, 2.25 eq) in water (365 ml) was added with a concomitant exotherm to 28° C. The phases were separated, and the aqueous phase was washed with toluene (95 ml). The organic phase was washed with water (315 ml), then concentrated under reduced pressure. Toluene (46 ml) and methanol (60 ml) were added, followed by palladium on carbon (5%, 50% water wet, 3.1603 g, 0.7426 mmol, 0.00469 eq), and the mixture was sealed in a Parr shaker. Hydrogen pressure (40 psi) was applied and maintained while agitating for 42 min. The catalyst then was removed by filtration under reduced pressure, and washed with toluene (60 ml). Heptane (150 ml) added to the filtrate and the resultant slurry concentrated under reduced pressure. Heptane (300 ml) was added, and the precipitate collected by filtration under reduced pressure, washed with heptane, and dried to give the title compound, HPLC (stationary phase is 4.6×250 mm Zorbax RX C-8 column; mobile phase is acetonitrile (650 ml), triethylamine (1.85 ml) and acetic acid (1.30 ml) and water of sufficient amount to make 1,000 ml; flow rate=3.0 ml/min; UV detection at 254 um) RT=1.08 min, >99.3 area); $^1$H-NMR (Pyridine-d$_5$) δ: 2.95–2.98, 3.80–3.83, 5.38, 6.68, 6.78 and 6.90; CMR (Pyridine-d$_5$) 52.43, 67.33, 103.31, 110.63, 121.29, 130.80, 146.23 and 157.72.

Step B: N-Carbomethoxy-3-fluoro-4-morpholinylaniline (Compound I, $R^1$=3-Fluoro-4-morpholinylphenyl)

3,4-Difluoronitrobenzene (24.967 g, 156.94 mmol) was added to a mixture of morpholine (60.0 ml, 688 mmol, 4.38 eq) in THF (30 ml) at −6° C. The mixture was permitted to warm to 10° over 2 hrs, then maintained at 10° C. for ½ hr. A mixture of citric acid monohydrate (75 g, 357 mmol, 2.27 eq) in water (365 ml) was added with concomitant exotherm to 280. The phases were separated, and the aqueous washed with toluene (95 ml). The organic phases were washed with water (315 ml), the aqueous back wash extracted with toluene (95 ml), and concentrated under reduced pressure. Toluene (76 ml) and methanol (60 ml) were added, followed by palladium on carbon (5%, 50% water wet, 3.1370 g, 0.7371 mmol, 0.00470 eq), and the mixture sealed in a Parr shaker. Hydrogen pressure (40 PSI) was applied and maintained while agitating for 4.5 hrs. The catalyst then was removed by filtration under reduced pressure, and washed with toluene (100 ml). The mixture was cooled to 2° C., and a mixture of aqueous potassium carbonate (47%, 17.1 ml, 85 mmol, 0.54 eq) and water (150 ml) was added. Methyl chloroformate (16.4 ml, 212 mmol, 1.35 eq) then was added while maintaining the temperature at about 3–3.5°. The resultant slurry was permitted to warm to 20–25° C., then stirred 17 hrs. The mixture is warmed to 75° to give a solution, then cooled to 46°, heptane (333 ml) added, then the mixture cooled to 0° C., the precipitate collected by filtration with reduced pressure, washed with heptane (100 ml cooled to 5° C.) then water (230 ml cooled to 5° C.), and dried to give Compound I, wherein $R^1$=3-fluoro-4-morpholinylphenyl, TLC (silica gel; methanol/methylene chloride, 5/95) Rf=0.74 (one spot); $^1$H-NMR (CDCl$_3$) δ: 3.03, 3.76, 3.86, 6.75, 6.87, 6.98, 7.27; CMR (CDC13) 51.18, 52.42, 67.03, 107.81, 114.56, 119.00, 133.25, 135.77, 154.07, 155.70.

Example 2

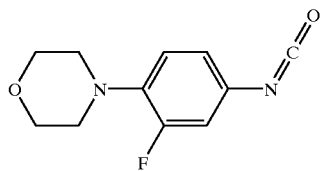

Preparation of 3-Fluoro-4-morpholinylphenylisocyanate (Compound VI, $R^1$=3-Fluoro-4-morpholinylphenyl)

A mixture of 3-fluoro-4-morpholinylaniline (Example 1, 12.01 g, 61.21 mmol) in methylene chloride (100 ml) was added to a mixture of phosgene (1.93 M in toluene, 63.4 ml, 122.4 mmol, 2.00 eq) in p-chlorotoluene (60 ml) over 15 min, while maintaining a temperature of about −12 to 3° C. The material was rinsed in with methylene chloride (30 ml). The mixture then was warmed to 130° C. under atmospheric pressure with concomitant distillation of methylene chloride, phosgene, toluene, and hydrogen chloride gas into a caustic scrubber. The mixture was cooled to 25° C. and filtered. The precipitate was washed with methylene chloride (3×15 ml). The filtrate was concentrated under reduced pressure. Heptane (200 ml) was added to the concentrated filtrate, and the resultant slurry cooled to −32° C. The product was collected by filtration with reduced pressure, washed with heptane, cooled to −30° C., and dried in a nitrogen stream to give Compound VI, wherein $R^1$=3-fluoro-4-morpholinylphenyl, HPLC (stationary phase is 4.6×250 mn Zorbax RX C-8 column; mobile phase is acetonitrile (650 ml), triethylamine (1.85 ml) and acetic acid (1.30 ml) and water of sufficient amount to make 1,000 ml; flow rate=3.0 ml/min; UV detection at 254 nm) RT=1.08 min. Upon derivatizing as N-carbomethoxy-3-fluoro-4-morpholinylaniline by dissolving in methanol; $^1$H-NMR (CDCl$_3$) δ: 3.05, 3.86 and 6.78–6.89; CMR (CDCl$_3$) 50.90, 66.89, 113.11, 119.15, 120.83, 124.67, 127.65, 138.06 and 155.40; MS (EI), m/z (relative intensity) 222 (37) and 164 (100).

Example 3

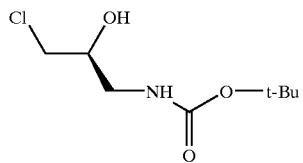

Preparation of Tert-Butyl (2S)-3-chloro-2-hydroxypropylcarbamate, Alternatively Named N-((2S)-3-chloro-2-hydroxypropyl)(tert-butoxy)carboxamide (Compound IV, $R^3$=t-butyl, X=Cl)

To a slurry of (2 S) 1-amino-3-chloro-2-propanol hydrochloride, (750.3 g, 5138 mmol) in methylene chloride (2728 g) and methanol (435.4 g) at −13° C. was added a solution of di-tert-butyldicarbonate (1178.3 g, 5399 mmol, 1.05 eq) in methylene chloride (1144 g) followed by triethylamine (572.3 g, 5656 mmol, 1.10 eq). The resultant 13° C. slurry was then warmed and stirred at 17–19° C. for 1 h. The resultant solution was concentrated under reduced pressure to a 2182 g slurry. Toluene (959.3 g) and water (975.5 g) were added and the phases separated. The organic phase was washed with water (500 ml) and the aqueous serial back extracted with toluene (2×500 ml). The combined organics were concentrated under reduced pressure to 1592 g. Isooctane (5853 g) was added and the mixture seeded and stirred at 20–25° C. for 17 h. The precipitated product was collected by vacuum filtration, washed with isooctane (400 g) and dried in a nitrogen stream to afford Compound IV, wherein $R^3$=t-butyl, X=Cl, (1024 g, 95.1%): GC retention time=8.2 min (15 meter DB5 capillary column, 70° C. for 2 min, then ramp 10° C./min); $^1$H-NMR (CDCl$_3$, 400 MHz) δ: 5.08 (bs, 1H), 3.92 (m, 2H), 3.57 (bs, 1H), 3.55 (m, 1H), 3.42 (m, 1H), 3.24 (m, 1H), 1.45 (s, 9H); $^{13}$C-NMR (CDCl$_3$, 100 MHz) d 28.35 (q), 43.90 (t), 46.52 (t), 71.23 (d), 80.13 (s), 157.24 (s).

Example 4

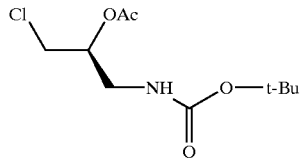

Preparation of (1S)-2-[(tert-butoxycarbonyl)amino]-1-(chloromethyl)ethyl Acetate, Alternatively Named N-((2S)-3-chloro-2-acetoxypropyl)(tert-butoxy)carboxamide (Compound V, $R^3$=t-butyl, $R^4$=Ac, X=Cl)

To a solution of tert-butyl (2S)-3-chloro-2-hydroxypropylcarbamate (0.9928 g, 4.74 mmol) in THF (7 ml) and triethylamine (0.7303 g, 7.22 mmol, 1.52 eq) was added acetic anhydride (0.6033 g, 5.91 mmol, 1.25 eq) and N, N-dimethyl-4-aminopyridine (0.00265 g, 0.0217 mmol, 0.0046 eq). The solution was stirred at room temperature for 3 days. Toluene (10 g) and saturated aqueous sodium bicarbonate (10 ml) was added and the phases separated. The aqueous was washed with a mixture of toluene (10 ml) and THF (5 ml) and the combined organics dried on magnesium sulfate. The organics were concentrated under reduced pressure to 1.6 g and heptane (7.3 g) added. After standing for 25 days at 20–25° C., a precipitate formed. Heptane (10.8 g) was added and the precipitate collected by vacuum filtration, washed with heptane (10 ml) and dried in a nitrogen stream to give Compound V, wherein $R^3$=butyl, $R^4$=Ac, X=Cl, 0.3803 g (31.9%): $^1$H-NMR (400 MHz, CDCl$_3$) δ: 1.45 (s, 9H), 2.11 (s, 3H), 3.41 (m, 2H), 3.67 (m, 2H), 4.79 (s, 1H), 5.07 (t, J=5.2 Hz, 1H); $^{13}$C NMR (CDCl$_3$) 20.92 (q), 28.33 (q), 41.43 (t), 43.30 (t), 72.16 (d), 79.89 (s), 155.85 (s), 170.26 (s); MS (El) for $C_{10}H_{18}ClNO_4$ m/z 251 M$^+$; $[α]^{22}_D$ (−2, C=1.0, methylene chloride); Anal. Calcd for $C_{10}H_{18}ClNO_4$: C, 47.72; H, 7.21; N, 5.57. Found: C, 47.70; H, 7.17; N, 5.55.

Example 5

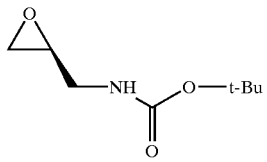

Preparation of Tert-Butyl (2S)oxiranylmethylcarbamate, Alternatively Named N-[((2S)oxiran-2-yl)methyl](tert-butoxy)carboxamide (Compound II, $R^3$=t-butyl, X=Cl)

To a solution of tert-butyl (2S)-3-chloro-2-hydroxypropylcarbamate (19.98 g, 95.29 mmol) in methanol (50.0 ml) at 13° C. was added lithium t-butoxide (8.40 g, 104.9 mmol, 1.10 eq) while maintaining less than 22° C. The mixture was stirred at 8 to 20° C. for 15 min and water (200 ml) followed by methylene chloride (200 ml) was added. The phases were separated and the aqueous washed with methylene chloride (135 ml). The combined organics were dried on magnesium sulfate and concentrated to an oil. Column chromatography on silica gel (0 to 4% methanol in methylene chloride eluent) gave Compound II, wherein $R^3$=t-butyl, X=Cl, as a white solid (14.26 g, 86.4%): m.p. 45–49° C.; $^1$H NMR (400 MHZ, CDCl$_3$) δ: 1.448 (s, 9H), 2.59 (s, 1H), 2.78 (t, J=4 Hz, 1H), 3.09 (s, 1H), 3.20 (dt, J=14.6 Hz, 1H), 3.53 (d, J=15 Hz, 1H), 4.85 (s, 1H); $^{13}$C NMR (CDCl$_3$) 28.28 (q), 41.72 (t), 45.04 (t), 50.85 (d), 79.61 (s), 155.96 (s); MS (Cl+) for $C_8H_{15}NO_3$ m/z 174 (M+H)$^+$; $[α]^{22}_D$ (−13, C+1.0, methylene chloride); Anal. Calcd for $C_8H_{15}NO_3$: C, 55.47; H, 8.73; N, 8.09. Found: C, 55.17; H, 8.54; N, 8.00.

Example 6

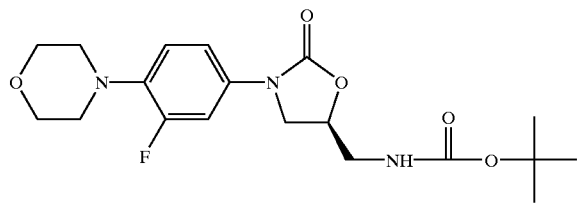

Preparation of Tert-Butyl {(5S)-3-[3-fluoro-4-(4-morpholinyl)phenyl]-2-oxo-1,3-oxazolidin-5-yl}methylcarbamate (Compound III, R=3-fluoro-4-(4-morpholinyl)phenyl, $R^3$=t-butyl)

To a solution of [3-fluoro-4-(4-morpholinyl)phenyl] carbamic acid phenylmethyl ester (Example 1) (0.8758 g, 2.651 mmol) and tert-butyl (2S)-chloro-2-hydroxypropylcarbamate (Example 3) (0.7011 g, 3.344 mmol, 1.26 eq) in DMF (1.7 ml) in an ice bath was added a solution of lithium t-butoxide in THF (2.82 g of an 18.1 wt % solution, 6.37 mmol, 2.40 eq). The resultant solution was allowed to stand at 20° C. for 44 hours (HPLC showed 95.0% conversion after 20 hours and 97.8% conversion after 44 hours). Saturated aqueous ammonium chloride (5.0 ml), water (10 ml) and methylene chloride (12 ml) were added and the phases separated. The aqueous layer was washed with methylene chloride (12 ml) and the combined organics dried on magnesium sulfate and concentrated to an oil (2.4574 g). External standard HPLC showed the oil to contain 0.9397 g (89.6%) of Compound III, wherein $R^1$=3-fluoro-4-(4-morpholinyl)phenyl, $R^3$=t-butyl. HPLC retention time=4.97 min (column=Zorbax SB-C8 3.5 micron 150×4.6 mm, flow rate=2.0 ml/min, gradient elution from 30:70 A:B to 90:10 A:B over 15 minutes; A=969:30:1 acetonitrile: THF: trifluoroacetic acid; B=949:50:1 water: THF: trifluoroacetic acid). An analytical sample of Compound III, $R^1$=3-fluoro-4-(4-morpholinyl)phenyl, $R^3$=t-butyl isolated by column chromatography (ethyl acetate/hexanes eluent) had the following physical properties: mp 46.2–48.0C; $^1$H-NMR (CDCl$_3$, 400 MHz) δ: 7.43 (dd, J=14.4, 2.4 Hz, 1H) 7.09 (dd, J=8.8, 2.0 Hz), 6.92 (t, J=9.2, 1H) 5.11 (bs, 1H), 4.73 (bs, 1H), 4.00 (t, J=8.8, 1H), 3.86 (t, J=4.4,4H), 3.80 (t, J=6.8, 1H), 3.50 (m, 2H), 3.04 (t, J=4.8, 4H), 1.41 (s, 9H); $^{13}$C-NMR (CDCl$_3$, 100 MHz) d 28.25 (q), 43.27 (t), 47.53 (t), 51.03 (dt, $J_{C-F}$=3.02 Hz), 66.95 (t), 71.99 (D), 80.19 (s), 107.50 (dd, $J_{C-F}$=26.16 Hz), 113.93 (dd, $J_{C-F}$=3.02 Hz), 118.83 (dd, $J_{C-F}$=4.03 Hz), 133.18 (sd, $J_{C-F}$=11.07 Hz), 136.45 (sd, $J_{C-F}$=9.06 Hz), 154.29 (s), 155.55 (sd, $J_{C-F}$=241.50 Hz), 156.30 (s). MS (EI) m/z (relative intensity) 395 (100), 339 (85); $[α]^{25}_D$-36 (C 0.71, acetonitrile); Anal Calcd for $C_{19}H_{26}FN_3O_5$: C, 57.71; H, 6.63; N, 10.63; found: C, 57.63; H, 6.81; N, 10.32.

Example 7

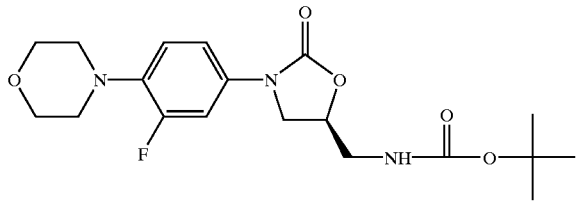

Alternative Preparation of Tert-Butyl {(5S)-3-[3-fluoro-4(4-morpholinyl)phenyl]-2-oxo-1,3-oxazolidin-5-yl}methylcarbamate (Compound III, $R^1$=3-fluoro-4-(4-morpholinyl)phenyl, $R^3$=t-butyl).

To a slurry of [3-fluoro-4(4-morpholinyl)phenyl]carbamic acid phenylmethyl ester (Example 1) (1.0039 g, 3.039 mmol) and tert-butyl (2S)oxiranylmethylcarbamate (Example 5) (0.653 g, 3.77 mmol, 1.24 eq) in THF (1.5 ml) at 0° C. was added a solution of lithium t-butoxide in THF (18.07 wt %, 1.735 g, 3.92 mmol, 1.29 eq). After standing 2 days at 20–25° C., methylene chloride (5.0 ml), then acetic acid (0.35 ml, 6.11 mmol, 2.01 eq) followed by water (3.5 ml) was added. The phases were separated and the aqueous washed with methylene chloride (3.5 ml). The combined organics were dried on magnesium sulfate and concentrated to an oil which was shown to contain 1.03 g (85.7%) of Compound III, wherein $R^1$=3-fluoro-4-(4-morpholinyl) phenyl, $R^3$=t-butyl, by external standard HPLC: retention time=4.06 min (column=Zorbax SB-C8 3.5 micron 150×4.6 mm, flow rate =2.0 ml/min; gradient elution from 30:70 A:B to 90:10 A:B over 15 minutes; A=969:30:1 acetonitrile: THF: trifluoroacetic acid; B=949:50:1 water: THF:trifluoroacetic acid).

Example 8

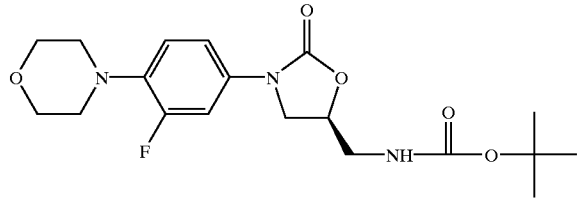

Alternative Preparation of Tert-Butyl {(5S)-3-[3-fluoro-4-(4-morpholinyl)phenyl]-2-oxo-1,3-oxazolidin-5-yl}methylcarbamate (Compound III, $R^1$=3-fluoro-4-(4-morpholinyl)phenyl, $R^3$=t-butyl)

To a solution of [3-fluoro-4-(4-morpholinyl)phenyl] carbamic acid phenylmethyl ester, (Example 1) (0.1646 g, 0.498 mmol) and (1S)-2-[(tert-butoxycarbonyl)amino]1-(chloromethyl) ethyl acetate, (Example 4) (0.1534 g, 0.609 mmol, 1.22 eq) in DMF (0.344 g) and methanol (0.0195 g, 0.609 mmol, 1.22 eq) at 0° C. was added lithium t-butoxide (0.0881 g, 1.101 mmol, 2.21 eq). The solution was allowed to stand at 20–25° C. for 18 h. Acetic acid (0.057 ml, 0.996 mmol, 2.00 eq) was added. The mixture was diluted to 250 ml total volume with methanol. The resultant solution was shown to contain 0.186 g (94.6%) of Compound III, wherein $R^1$=3-fluoro-4-(4-morpholinyl)phenyl, $R^3$=t-butyl by external standard HPLC: retention time=4.10 min (column=Zorbax SB-C8 3.5 micron 150×4.6 mm, flow rate=2.0 ml/min., gradient elution from 30:70 A:B to 90:10 A:B over 15 minutes; A=969:30:1 acetonitrile: THF: trifluoroacetic acid; B=949:50:1 water: THF: trifluoroacetic acid).

Example 9

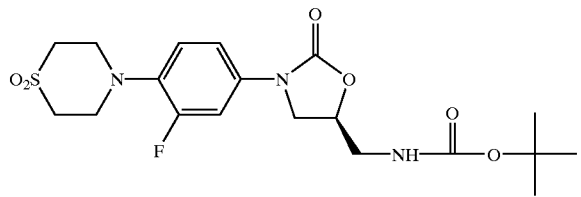

Preparation of Tert-Butyl {(5S)-3-[4-(1,1-dioxohexahydro-1$\lambda^6$-thiopyran-4-yl)-3-fluorophenyl)-2-oxo-1,3-oxazolidin-5-yl}methylcarbamate (Compound III, $R^1$4-(1,1-dioxohexahydro-1$\lambda^6$-thiopyran-4-yl)-3-fluorophenyl, $R^3$=t-butyl)

To a slurry of isobutyl 4-(1,1-dioxohexahydro-1$\lambda^6$-thiopyran-4-yl)-3-fluorophenylcarbamate (1.0037 g, 2.92 mmol), and tert-butyl (2S)-3-chloro-2-hydroxypropylcarbamate (Example 3) (0.7608 g, 3.629 mmol, 1.24 eq) in DMF (1.80 ml) in an ice bath was added lithium t-butoxide in THF (18.07 wt % solution, 2.7465 g, 6.20 mmol, 2.12 eq). The mixture was allowed to stand at 20–25° C. for 37 h. Toluene (10 ml), saturated aqueous ammonium chloride (5 ml), water (5 ml) and heptane (10 ml) were added and the precipitate collected by vacuum filtration, washed with water (13.2 g) and toluene (10.2 g) and dried in a nitrogen stream to afford Compound III, wherein $R^1$=4-(1,1-dioxohexahydro-1$\lambda^6$-thiopyran-4-yl)-3-fluorophenyl, $R^3$=t-butyl, 1.1507 g (89.0%). HPLC retention time=3.0 min (column=phenomenex Luna C8 5 micron, 150×4.6 m, flow rate=2.0 ml/min, gradient elution from 40:60 A:B to 100:0 A:B over 15 minutes; A=acetonitrile; B=water).

Example 10

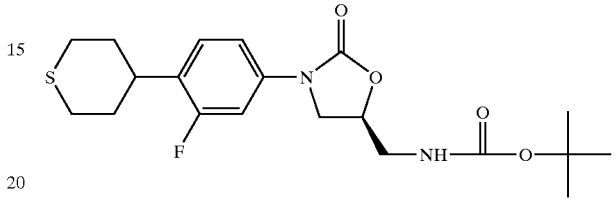

Preparation of Tert-Butyl [(5S)-3-(3-fluoro-4-tetrahydro-2H-thiopyran-4-ylphenyl)-2-oxo-1,3-oxazolidin-5-yl] methylcarbamate (Compound III, $R^1$=3-fluoro-4-tetrahydro-2H-thiopyran-4-ylphenyl, $R^3$=t-butyl)

To a slurry of isobutyl 3-fluoro-4-tetrahydro-2H-thiopyran-4-ylphenylcarbamate (0.9142 g, 2.936 mmol) and tert-butyl (2S)-3-chloro-2-hydroxypropylcarbamate (Example 3) (0.7676 g, 3.661 mmol, 1.25 eq) in DMF (1.80 ml) in an ice bath was added lithium t-butoxide in THF (18.07 wt % solution, 3.31 g, 7.46 mmol, 2.54 eq). The mixture was allowed to stand at 20–25° C. for 1 day. Saturated aqueous ammonium chloride (5 ml), water (5 ml) and methylene chloride were added and the phases separated. The aqueous was washed with methylene chloride (12 ml) and the combined organics dried on magnesium sulfate. Toluene (20 ml) was added to the organics and the solution concentrated under reduced pressure to give the Compound III, wherein $R^1$=3-fluoro-4-tetrahydro-2H-thiopyran-4-ylphenyl, $R^3$=t-butyl, HPLC retention time 7.1 min (column=phenomenex Luna C8, 5 micron 150×4.6 mm, flow rate 2.0 ml/min, gradient elution from 40:60 A:B to 100:0 A:B over 15 minutes; A=acetonitrile; B=water).

Example 11

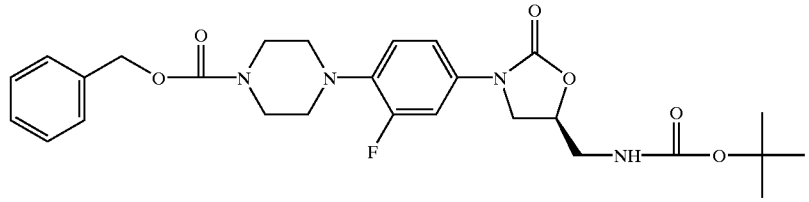

Preparation of Benzyl 4–14-((5S)-5{[(tert-butoxycarbonyl)amino]methyl}-2-oxo-1,3-oxazolidin-3-yl)-2-fluorophenyl]-1-piperazinecarboxylate (Compound III, $R^1$=3-fluoro-4-[4-(benzyloxycarbonyl)-1-piperazinyl] phenyl, R=t-butyl)

To a slurry of 4-[2-fluoro-4-[[(phenylmethoxy)carbonyl] amino]phenyl]-1-piperazinecarboxylic acid phenylmethyl ester (552.5 g, 1.19 mol) and tert-butyl (2S)-3-chloro-2-hydroxypropylcarbamate (Example 3) (460.8 g, 2.38 mol, 2.0 eq) in DMF (925 ml), methanol (96.4 ml, 2.38 mol, 2.0 eq), hexane (451 ml) and toluene (537 ml) was added a solution of lithium t-butoxide (285.5 g, 3.57 mmol, 3.0 eq) in hexanes rinse (1326) ml over 1.5 hours while maintaining about 15° C. and followed by hexanes rinse (50 ml). The mixture was then stirred at room temperature overnight at 20–25° C. The mixture was cooled to 0° C. and acetic acid (142.9 g, 2.38 moles, 2 eq) added. Methanol (290 ml) was added and the phases separated. The upper phase was washed twice with methanol (290 ml) and to the combined lower phases added methylene chloride (1300 ml) and water (1300 ml). The phases were separated and the upper phase washed twice with methylene chloride (300 ml). The combined lower phases were concentrated under reduced pressure to 2000 ml and methanol (650 ml) was added. The mixture was concentrated to 1500 ml and toluene (630 ml) and water (650 ml) added over ½ h. Hexanes (550 ml) were added slowly and the slurry cooled to 0° C. and stirred 1.5 h. The precipitate was collected by vacuum filtration and washed with water and hexanes. A second crop was collected upon concentrating the filtrate. Both crops were triturated with cold methyl t-butyl ether and dried under reduced pressure to give Compound III, wherein $R^1$=3-fluoro-4-[4-(benzyloxycarbonyl)-1-piperazinyl]phenyl, $R^3$=t-butyl, 493 g (78.2%): $^1$H NMR (400 MHz, CDCl$_3$) δ: 1.405 (s, 9H), 3.004 (s, 4H), 3.52 (q, J=5, 5 Hz, d H), 3.52 (q, J=5 Hz, 2H), 3.67 (t, J=5 Hz, 4H), 3.80 (t, J=7 Hz, H), 3.99 (t, J=9 Hz, 1H), 4.73 (m, 1H), 4.98 (m, 1H), 5.16 (s, 2H), 6.90 (t, J=9 Hz, 1H), 7.09 (dd, J=2.9 Hz, 1H), 7.34 (m, 1H), 7.37 (d, J=4 Hz, 4H), 7.43 (dd, J=2.14 Hz, 1H).

Example 12

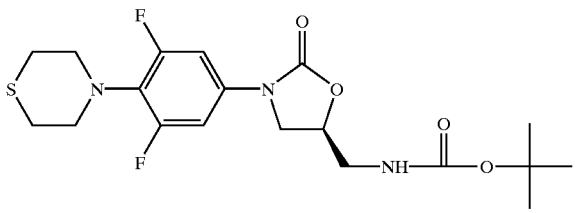

Preparation of Tert-Butyl {(5S)-3-[3,5-difluoro-4-(4-thiomorpholinyl)phenyl]-2-oxo-1,3-oxazolidin-5-yl}methylcarbamate (Compound III, $R^1$=3,5-difluoro-4-(4-thiomorpholinyl)phenyl, $R^3$=t-butyl)

To a solution of benzyl 3,5-difluoro-4-(4-thiomorpholinyl)phenyl-carbamate (0.953 g, 2.61 mmol) and tert-butyl (2S)-3-chloro-2-hydroxypropyl-carbamate (Example 3) (0.690 g, 3.29 mmol, 1.26 eq) in DMF (3.4 ml) at 0° C. was added a solution of lithium t-butoxide in hexanes (1.0 M, 6.26 ml, 6.26 mmol, 2.40 eq). The mixture was stirred for 1 day at 20–25° C. and DMF (0.5 ml) added. The mixture was partitioned between aqueous ammonium chloride and methylene chloride. The aqueous was washed 6 times with methylene chloride, dried on sodium sulfate and concentrated to a brown oil. The resulting oil was purified by column chromatography (ethyl acetate/hexanes/methanol eluent) to afford Compound III, wherein $R^1$=3,5-difluoro-4-(4-thiomorpholinyl)phenyl, $R^3$=t-butyl, 0.457 g, (41%): Silica gel TLC $R_f$=0.38 (5:95 methanol: methylene chloride); $^1$H NMR (400 MHz, CDCl$_3$) δ: 1.42 (s, 9H), 2.75 (s, 4H), 3.36 (t, J=4 Hz, 4H), 3.52 m, 2H), 3.79 (t, J=7 Hz, 1H), 3.97 (t, J=9 Hz, 1H), 4.74 (m, 1H), 4.94 (m, 1H), 7.10 (d, J=11 Hz, 2H); MS (ESI+) for C$_{19}$H$_{25}$F$_2$N$_3$O$_4$S m/z 430 (M+H)$^+$, 452 (M+Na)$^+$.

Example 13

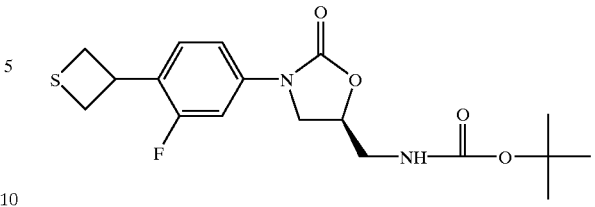

Preparation of Tert-Butyl {(5S)-3-[3-fluoro-4-(3-thietanyl)phenyl]-2-oxo-1,3-oxazolidin-5-yl}methylcarbamate (Compound III, $R^1$=3-fluoro-4-(3-thietanyl)phenyl, $R^3$=t-butyl)

To a solution of benzyl 3-fluoro-4-(3-thietanyl)phenylcarbamate (0.406 g, 1.28 mmol) and tert-butyl (2S)-3-chloro-2-hydroxypropylcarbamate (Example 3) (0.322 g, 1.54 mmol, 1.2 eq) in DMF (1 ml) in an ice bath was added a solution of lithium t-butoxide in THF (1 M, 3.1 ml, 3.1 mmol, 2.4 eq). The resultant solution was stirred at room temperature for 1 day. The mixture was partitioned between aqueous ammonium chloride and methylene chloride. The aqueous was washed 3 times with methylene chloride, dried on sodium sulfate and concentrated to a brown oil. The resulting oil was purified by column chromatography (ethyl acetate/hexanes eluent) to afford Compound III, wherein $R^1$=3-fluoro-4-(3-thietanyl)phenyl, $R^3$=t-butyl, 0.360 g, (73.5%): Silica gel TLC $R_f$=0.28 (30:70 ethyl acetate: hexanes); $^1$H NMR (400 MHz, CDCl$_3$) δ: 1.41 (s, 9H), 3.36 (t, J=9 Hz, 2H), 3.54 (m, 2H), 3.62 (+, J=9 Hz, 2H), 3.843 (+, J=7 Hz, I H), 4.02 (+, J=9 Hz, 1H), 4.78 (m, 2 H), 4.95 (s, 1H), 7.21 (d, J=9 Hz, 1H), 7.37 (d, J=8 Hz, 1H), 7.42 (d, J=10 Hz, 1 H); MS (ESI+) for C$_{18}$H$_{23}$FN$_2$O$_4$S m/z 405 (M+Na)$^+$.

Example 14

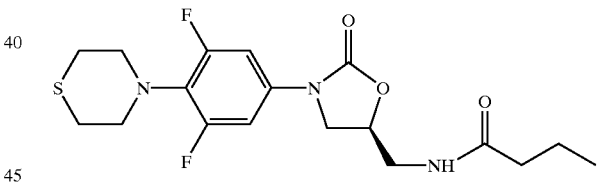

Preparation of N-({5S)-3-[3,5-difluoro-4-(4-thiomorpholinyl)phenyl]-2-oxo-1,3-oxazolidin-5-yl}methyl)propanamide (Compound X, $R^1$=3,5-difluoro-4-(4-thiomorpholinyl)phenyl, $R^5$=propionyl)

To a solution of tert-butyl {5S)-3-[3,5-difluoro-4-(4-thiomorpholinyl)phenyl]-2-oxo-1,3-oxazolidin-5-yl}methylcarbamate (Example 12) (0.457 g, 1.06 mmol) in methylene chloride (10 ml) was added trifluoroacetic acid (5 ml). After 1 h at 20 to 25° C., the reaction mixture was concentrated under reduced pressure. Methylene chloride (10 ml), pyridine (1.0 ml) and propionic anhydride (0.84 ml, 5.4 mmol, 6 eq) were added and the mixture stirred for 20 h at 20–24° C. Methylene chloride and aqueous hydrochloric acid (1 M) were added and the phases separated. The organics were washed with hydrochloric acid (1 M) until acidic. The combined organics were washed with aqueous sodium, bicarbonate and saturated aqueous sodium chloride solutions, dried on sodium sulfate, and concentrated to give Compound X, wherein $R^1$=3,5-difluoro-4-(4-thiomorpholinyl)phenyl, $R^5$=propionyl as a white solid (0.388 g, 94.8%); $^1$H NMR (400 MHz, CDCL$_3$) 1.13 (t, J=8

Hz, 3H), 2.25 (q, J=7 Hz, 2H), 2.28 (s, 4H), 3.36 (s, 4H), 3.70 (m, 3H), 3.99 (t, J=9 Hz, 1H), 4.77 (m, 1H), 5.91 (s, 1H), 7.09 (m, 2H).

Example 15

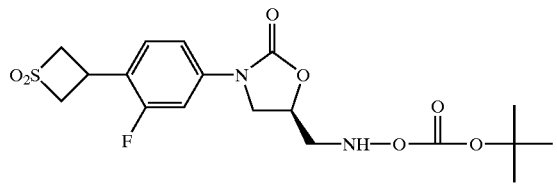

Preparation of Tert-Butyl {(5S)-3-[4-(1,1-dioxido-3-thietanyl)-3-fluorophenyl]=2-oxo-1,3-oxazolidin-5-yl}methylcarbamate (Compound III, $R^1$=4-(1,1-dioxido-3-thietanyl)-3-fluorophenyl, $R^3$=t-butyl)

To a mixture of tert-butyl {(5S)-3-[3-fluoro-4-(3-thietanyl)phenyl}-2-oxo-1,3-oxazolidin-5-yl}methylcarbamate (Example 13) (0.155 g, 0.41 mmol), water (1.25 ml) and acetone (3.75 ml) was added N-methylmorpholine-N-oxide (0.145 g, 1.21 mmol, 3.0 eq) and a solution of osmium tetroxide in tertiary butyl alcohol (0.080 M, 0.1 ml, 0.008 mmol, 0.02 eq). The mixture was stirred for 24 h at 20–25° C. and saturated aqueous sodium busulfite (20 ml) was added. The reaction mixture was extracted with methylene chloride (3×20 ml), the combined organicswashed with saturated aqueous sodium chloride (3×10 ml), water (3×10 ml), and dried over sodium sulfate. Silica gel chromatography (methanol/methylene chloride eleuent) gave Compound III, wherein $R^1$=4-(1,1-dioxido-3-thietanyl)-3-fluorophenyl, $R^3$=t-butyl (0.134 g, 78%):silica gel TLC $R_f$=0.67(5% methanol/methylene chloride); $^1$H NMR (400 MHz, CDCl$_3$) 1.41 (s, 9H), 3.50 (m, 2H), 3.86 (t, J=7 Hz, 1H), 23 Hz, 2H), 3.97 (t, J=9 Hz, 1H), 4.03 (t, J=9 Hz, 1H), 4.29 (dd, J=8, 11 Hz, 2H), 4.51 (dd, J=9, 23 Hz, 2H), 4.78 (m, 1H), 5.01 (s, 1H), 7.22 (dd, J=2, 10 Hz, 1H), 7.35 (m, 1H), 7.55(dd, J-2, 13 Hz, 1H); MS (ESI−) m/z (413, M−H).

Example 16

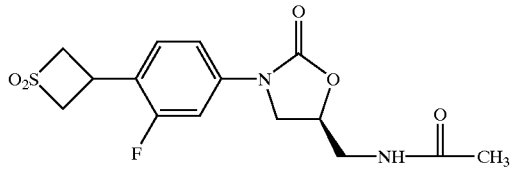

Preparation of N-({5S)-3-[4-(1,1-dioxido-3-thietanyl)-3-fluorophenyl]-2-oxo-1,3-oxazolidin-5-yl}methyl)acetamide (Compound X, $R^1$=4-(1,1-dioxido-3-thietanyl)-3-fluorophenyl, $R^5$=acetyl)

To a solution of tert-butyl {(5S)-3-[4-(1,1-dioxido-3-thietanyl)-3-fluorophenyl}-2-oxo-1,3-oxazolidin-5-yl}methylcarbamate (Example 15) (0.134 g, 0.32 mmol) in methylene chloride (2 ml) was added hydrochloric acid (4 M, 3 ml, 12 mmol). The mixture was stirred for 3 h at 20 to 25° C. and concentrated under reduced pressure. The product was extracted with methylene chloride (2×3 ml) and pyridine (0.26 ml, 3.2 mmol, 10 eq) was added followed by acetic anhydride (0.15 ml, 1.6 mmol, 5 eq). The mixture was stirred at 20 to 25° C. for 2 h and methylene chloride (40 ml) was added. The solution was washed with hydrochloric acid (1%, 3×10 ml), saturated aqueous sodium chloride (3×10 ml), water (3×10 ml), and dried over sodium sulfate. Silica gel chromatography (methanol/methylene chloride eleuent) gave Compound X, wherein $R^1$=4-(1,1-dioxido-3-thietanyl)-3-fluorophenyl, $R^5$=acetyl (0.085 g, 75.0%):silica gel TLC $R_f$=0.4 (5% methanol/methylene chloride); $^1$H NMR (400 MHz, CDCl$_3$) 2.03 (s, 3H), 3.66 (m, 2H), 3.80 (t, J=7 Hz, 1H), 3.98 (t, J=9 Hz, 1H), 4.06 (t, J=9 Hz, 1H), 4.304 (t, J=8 Hz, 2H), 4.50 (t, J 14 Hz, 2H), 4.80 (m, 1H), 6.07 (s, 1H), 7.21 (d, J 9 Hz, 1H), 7.37 (t, J=9 Hz, 1H), 7.54 (d, J=13 Hz, 1H): MS (ESI+) m/z (357, M+H)$^+$.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of preparing an (S)-oxazolidinone having a general structural formula:

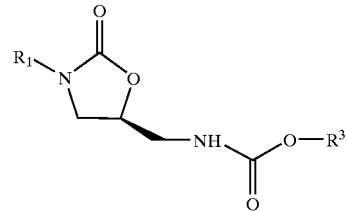

wherein $R^3$ is $C_1$–$C_{10}$ alkyl, and $R^1$ is optionally substituted aryl, or a salt or hydrate thereof, comprising contacting a carbamate having a general structural formula:

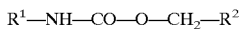

$$R^1\text{—NH—CO—O—CH}_2\text{—}R^2$$

wherein $R^2$ is selected from the group consisting of $C_1$–$C_{20}$ alkyl, $C_3$–$C_7$ cycloalkyl, phenyl optionally substituted with one or two $C_1$–$C_3$ alkyl or halogen groups, allyl, 3-methylallyl, 3,3-dimethylallyl, vinyl, styrylmethyl, benzyl optionally substituted on the phenyl with one or two Cl, $C_1$–$C_4$ alkyl, nitro, cyano, or trifluoromethyl groups, 9-fluorenylmethyl, trichloromethylmethyl, 2-trimethylsilylethyl, phenylethyl, 1-adamantyl, diphenylmethyl, 1,1-dimethylpropargyl, and isobornyl, or a salt or hydrate thereof, with i) a secondary alcohol having a general structural formula:

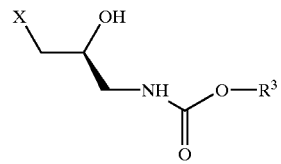

wherein X is halogen, alkylsulfonyloxy, or arylsulfonyloxy, or a salt or hydrate thereof made by the process comprising contacting an (S)-3-carbon amino alcohol having a general structural formula:

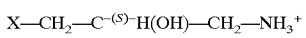

$$X\text{—CH}_2\text{—C}^{-(S)}\text{—H(OH)—CH}_2\text{—NH}_3^+$$

with a base and an carbonylating agent selected from the group consisting of a haloformate having a formula R³O—CO—X and a dialkyldicarbonate having a formula R³OCO₂R³;

ii) an (S)-epoxide having a general structural formula:

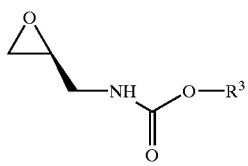

made by the process comprising contacting an (S)-secondary alcohol having a general structural formula:

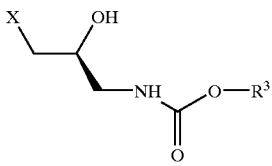

with a base and an acylating agent selected from the group consisting of an acid anhydride having a formula O(R⁴)₂, and an activated acid having a formula R⁴X; or iii) an (S)-ester having a general structural formula:

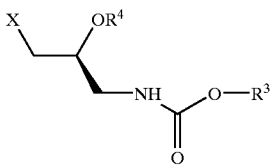

wherein R⁴ is C₁–C₅ alkylcarbonyl made by the process comprising contacting a) an (S)-secondary alcohol having a general structural formula:

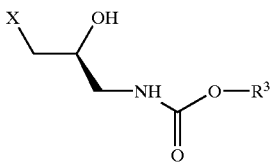

wherein X is a halogen, alkylsulfonyloxy, or arylsulfonyloxy; or b) an (S)-ester having a general structural formula:

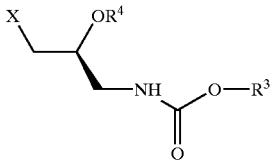

wherein R⁴ is C₁–C₅ alkylcarbonyl, with a lithium cation and a base whose conjugate acid has a pKa of greater than about 8;

in the presence of a lithium cation and a base whose conjugate acid has a pKa of greater than about 8.

2. The method of claim 1 of preparing an (S)-oxazolidinone having a general structural formula:

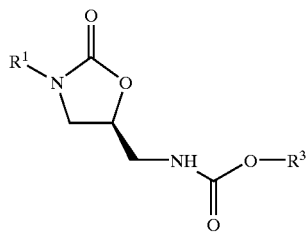

wherein R³ is C₁–C₁₀ alkyl, and R¹ is optionally substituted aryl, or a salt or hydrate thereof, comprising contacting a carbamate having a general structural formula:

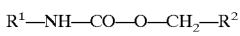

R¹—NH—CO—O—CH₂—R² wherein R² is selected from the group consisting of C₁–C₂₀ alkyl, C₃–C₇ cycloalkyl, phenyl optionally substituted with one or two C₁–C₃ alkyl or halogen groups, allyl, 3-methylallyl, 3,3-dimethylallyl, vinyl, styrylmethyl, benzyl optionally substituted on the phenyl with one or two Cl, C₁–C₄ alkyl, nitro, cyano, or trifluoromethyl groups, 9-fluorenylmethyl, trichloromethylmethyl, 2-trimethylsilylethyl, phenylethyl, 1-adamantyl, diphenylmethyl, 1,1-dimethylpropargyl, and isobornyl, or a salt or hydrate thereof, with i) a secondary alcohol having a general structural formula:

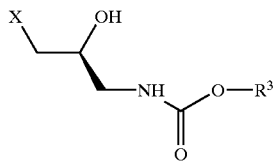

wherein X is halogen, alkylsulfonyloxy, or arylsulfonyloxy, or a salt or hydrate thereof;

ii) an (S)-epoxide having a general structural formula:

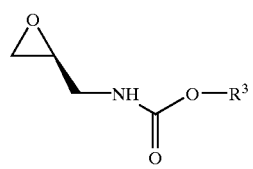

or iii) an (S)-ester having a general structural formula:

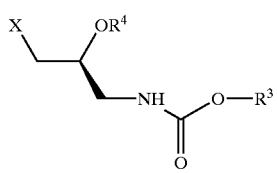

wherein R⁴ is C₁–C₅ alkylcarbonyl; in the presence of a lithium cation and a base whose conjugate acid has a pKa of greater than about 8.

3. The method of claim 2 further comprising isolating the (S)-oxazolidonone in a crystalline form.

4. The method of claim 2 wherein $R^1$ is:

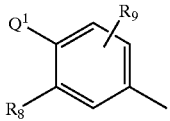

wherein $Q^1$ is: $R^{10}R^{11}N$,

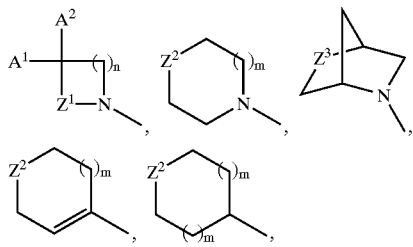

or $Q^1$ and $R^8$ taken together are dihydropyrrolidine, optionally substituted with $R^{12}$;

$Z^1$ is $CH_2(CH_2)_p$, $CH(OH)(CH_2)_p$, or $C(O)$;

$Z^2$ is $(O)_pS$, O, or $N(R^{13})$;

$Z^3$ is $(O)_pS$ or O;

$A^1$ is H or $CH_3$;

$A^2$ is selected from the group consisting of:
a) H,
b) HO,
c) $CH_3$,
d) $CH_3O$,
e) $R^{14}OCH_2$=C(O)NH,
f) $R^{15}OC(O)NH$,
g) $(C_1-C_3)$alkoxycarbonyl,
h) $HOCH_2$,
i) $CH_3ONH$,
j) $CH_3C(O)$,
k) $CH_3C(O)CH_2$,
l) $CH_3C(OCH_2CH_2O)$, and
m) $CH_3C(OCH_2CH_2O)CH_2$, or $A^1$—C—$A^2$ taken together are $CH_3$-C(OCH$_2$CH$_2$O), C(O), or C(=NR$^{22}$);

$R^8$ is H or F, or is taken together with $Q^1$ as above;

$R^9$ is H or F;

$R^{10}$ and $R^{11}$ are taken together with the N atom to form a 3,7-diazabicyclo[3.3.0]octane, pyrrole, pyrazole, imidazole, 1,2,3-triazole, 1,2,4-triazole, morpholine or a piperazine group, optionally substituted with $R^{13}$;

$R^{12}$ is selected from the group consisting of:
a) $CH_3C(O)$—,
b) HC(O)—,
c) $Cl_2CHC(O)$—,
d) $HOCH_2C(O)$—,
e) $CH_3SO_2$—,
f) $F_2CHC(O)$—,
g) $H_3CC(O)OCH_2C(O)$—,
h) $HC(O)OCH_2C(O)$—,
i) $R^{21}C(O)OCH_2C(O)$—,
j) $H_3CCHCH_2OCH_2C(O)$—,
k) benzylOCH$_2$C(O)—,
l)–m)

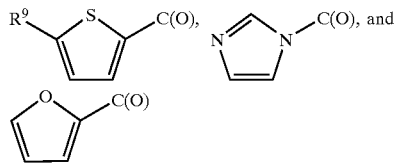

$R^{13}$ is selected from the group consisting of:
a) $R^{14}OC(R^{16})(R^{17})C(O)$—,
b) $R^{15}OC(O)$—,
c) $R^{18}C(O)$—,
d) $H_3CC(O)(CH_2)_2C(O)$,
e) $R^{19}SO_2$—,
f) $HOCH_2C(O)$—,
g) $R^{20}(CH_2)_2$—,
h) $R^{21}C(O)OCH_2C(O)$—,
i) $(CH_3)_2NCH_2C(O)NH$—,
j) $NCCH_2$—,
k) $F_2CHCH_2$,
l)–m

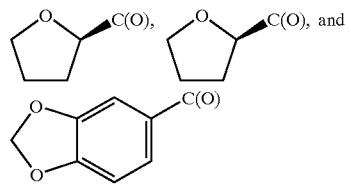

$R^{14}$ is H, $CH_3$, benzyl, or $CH_3C(O)$—;

$R^{15}$ is $(C_1-C_3)$alkyl, aryl, or benzyl;

$R^{16}$ and $R^{17}$, independently, are H or $CH_3$;

$R^{18}$ is selected from the group consisting of:
a) H—,
b) $(C_1-C_4)$alkyl,
c) aryl(CH$_2$)$_m$,
d) $ClH_2C$—,
e) $Cl_2HC$—,
f) $FH_2C$—,
g) $F_2HC$—, and
h) $(C_3-C_6)$cycloalkyl;

$R^{19}$ is selected from the group consisting of:
a) $CH_3$,
b) $CH_2Cl$,
c) $CH_2CH=CH_2$,
d) aryl, and
e) $CH_2CN$;

$R^{20}$ is OH, $CH_3O$—, or F;

$R^{21}$ is:
a) $CH_3$—,
b) $HOCH_2$—,
c) aniline, or
d) $(CH_3)_2N$—$CH_2$—, $R^{22}$ is selected from the group consisting of:
a) HO—
b) $CH_3O$—
c) $H_2N$—
d) $CH_3OC(O)O$—,
e) $CH_3C(O)OCH_2C(O)O$—,
f) aryl-$CH_2OCH_2C(O)O$—,
g) $HO(CH_2)_2O$—,
h) $CH_3OCH_2O(CH_2)_2O$—, and
i) $CH_3OCH_2O$—;

m is 0 or 1;

n is 1–3;

p is 0–2; and aryl is unsubstituted phenyl or phenyl unsubstituted with one of the following:
  a) F,
  b) Cl,
  c) OCH$_3$,
  d) OH,
  e) NH$_2$,
  f) (C$_1$–C$_4$)alkyl,
  g) OC(O)OCH$_3$, or
  h) NO$_2$;

and protected forms thereof.

5. The method of claim 4 wherein R$^1$ is selected from the group consisting of 3-fluoro-4-[4-(benzyloxycarbonyl)-1-piperazinyl]phenyl, 3-fluoro-4-(4-morpholinyl)phenyl, 4-(1,1-dioxohexahydro-1λ$^6$-thiopyran-4-yl)-3-fluorophenyl, 3-fluoro-4-tetrahydro-2H-thiopyran-4-ylphenyl, 3,5-difluoro-4-(4-thiomorpholinyl)phenyl, 3-fluoro-4-(3-thietanyl)phenyl, and 4-(1,1-dioxido-3-thietanyl)-3-fluorophenyl.

6. The method of claim 2 where R$^3$ is C$_4$–C$_7$ tertiary alkyl.

7. The method of claim 6 where R$^3$ is tertiary butyl.

8. The method of claim 2 where R$^2$ is methyl.

9. The method of claim 2 where X is Cl.

10. The method of claim 2 wherein the (S)-oxazolidinone is (S)-N-[[3-(3-fluoro-4-morpholinylphenyl)-2-oxo-5-oxazolidinyl]methyl]t-butoxycarbamide.

11. The method of claim 1 of preparing an (S)-oxazolidinone having a general structural formula:

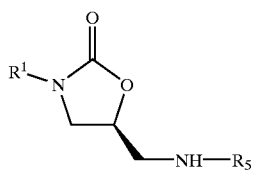

wherein R$^5$ is C$_1$–C$_6$ alkylcarbonyl, C$_1$–C$_6$ cycloalkylcarbonyl, C$_1$–C$_6$ alkylthiocarbonyl, or C$_1$–C$_6$ cycloalkylthiocarbonyl, and R$^1$ is optionally substituted aryl, or a salt or hydrate thereof, comprising:

(a) contacting a carbamate having a general formula

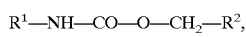

R$^1$—NH—CO—O—CH$_2$—R$^2$, wherein R$^2$ is selected from the group consisting of C$_1$–C$_{20}$ alkyl, C$_3$–C$_7$ cycloalkyl, phenyl optionally substituted with one or two C$_1$–C$_3$ alkyl or halogen groups, allyl, 3-methylallyl, 3,3-dimethylallyl, vinyl, styrylmethyl, benzyl optionally substituted on the phenyl with one or two Cl, C$_1$–C$_4$ alkyl, nitro, cyano, or tri-fluoromethyl groups, 9-fluorenylmethyl, trichloromethylmethyl, 2-trimethyl-silylethyl, phenylethyl, 1-adamantyl, diphenylmethyl, 1,1-dimethylpropargyl, , and isobornyl, ; with i) a secondary alcohol of a general structural formula:

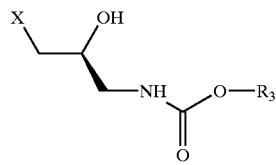

wherein X is a halogen, alkylsulfonyloxy, or arylsulfonyloxy, and R$^3$ is C$_1$–C$_{10}$ alkyl; or ii) an epoxide having a general structural formula:

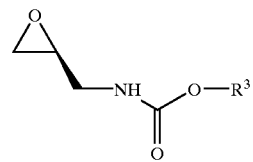

in the presence of a lithium cation and a base whose conjugate acid has a pKa of greater than about 8, to provide a ring-t-butylcarbamyl compound of a general structural formula:

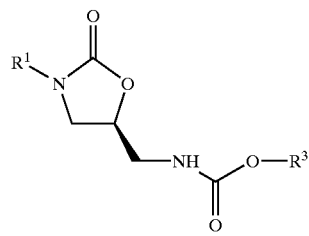

(b) contacting the reaction product of step (a) with aqueous acid; and (c) contacting the reaction product of step (2) with a base and an acylating or thioacylating agent selected from the group consisting of (i) an acid anhydride of the structural formula O(R$^5$)$_2$, (ii) an activated acid of the structural formula R$^5$X, or (iii) a dithioester of the structural formula R$^5$S(C=S)R$^5$, wherein R$^5$ is C$_1$–C$_6$ alkylcarbonyl, C$_1$–C$_6$ cycloalkylcarbonyl, C$_1$–C$_6$ alkylthiocarbonyl, or C$_1$–C$_6$ cycloalkylthiocarbonyl, and X is halogen, alkylsulfonyloxy, or arylsulfonyloxy.

12. The method of claim 11 further comprising isolating the (S)-oxazolidonone in a crystalline form.

13. The method of claim 11 wherein R$^1$ is:

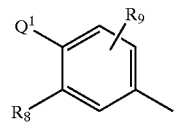

wherein Q$^1$ is: R$^{10}$R$^{11}$N,

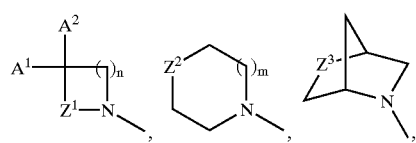

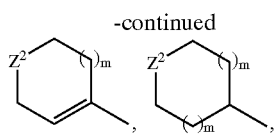

or $Q^1$ and $R^8$ taken together are dihydropyrrolidine, optionally substituted with $R^{12}$;

$Z^1$ is $CH_2(CH_2)_p$, $CH(OH)(CH_2)_p$, or $C(O)$;
$Z^2$ is $(O)_pS$, $O$, or $N(R^{13})$;
$Z^3$ is $(O)_pS$ or $O$;
$A^1$ is H or $CH_3$;
$A^2$ is selected from the group consisting of:
  a) H,
  b) HO,
  c) $CH_3$,
  d) $CH_3O$,
  e) $R^{14}OCH_2$=$C(O)NH$,
  f) $R^{15}OC(O)NH$,
  g) $(C_1-C_3)$alkoxycarbonyl,
  h) $HOCH_2$,
  i) $CH_3ONH$,
  j) $CH_3C(O)$,
  k) $CH_3C(O)CH_2$,
  l) $CH_3C(OCH_2CH_2O)$, and
  m) $CH_3C(OCH_2CH_2O)CH_2$,
or $A^1$—C—$A^2$ taken together are $CH_3$—$C(OCH_2CH_2O)$, $C(O)$, or $C(=NR^{22})$;

$R^8$ is H or F, or is taken together with $Q^1$ as above;
$R^9$ is H or F;
$R^{10}$ and $R^{11}$ are taken together with the N atom to form a 3,7-diazabicyclo[3.3.0]octane, pyrrole, pyrazole, imidazole, 1,2,3-triazole, 1,2,4-triazole, morpholine or a piperazine group, optionally substituted with $R^{13}$;
$R^{12}$ is selected from the group consisting of:
  a) $CH_3C(O)$—,
  b) $HC(O)$—,
  c) $Cl_2CHC(O)$—,
  d) $HOCH_2C(O)$—,
  e) $CH_3SO_2$—,
  f) $F_2CHC(O)$—,
  g) $H_3CC(O)OCH_2C(O)$—,
  h) $HC(O)OCH_2C(O)$—,
  i) $R^{21}C(O)OCH_2C(O)$—,
  j) $H_3CCHCH_2OCH_2C(O)$—,
  k) benzyl$OCH_2C(O)$—,
  l)-m)

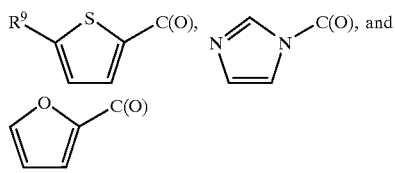

$R^{13}$ is selected from the group consisting of:
  a) $R^{14}OC(R^{16})(R^{17})C(O)$—,
  b) $R^{15}OC(O)$—,
  c) $R^{18}C(O)$—,
  d) $H_3CC(O)(CH_2)_2C(O)$,
  e) $R^{19}SO_2$—,
  f) $HOCH_2C(O)$—,
  g) $R^{20}(CH_2)_2$—,
  h) $R^{21}C(O)OCH_2C(O)$—,
  i) $(CH_3)_2NCH_2C(O)NH$—,
  j) $NCCH_2$—,
  k) $F_2CHCH_2$,
  l)-m)

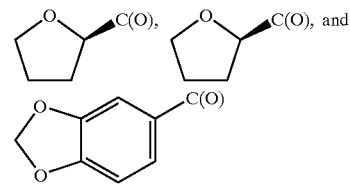

$R^{14}$ is H, $CH_3$, benzyl, or $CH_3C(O)$—;
$R^{15}$ is $(C_1-C_3)$alkyl, aryl, or benzyl;
$R^{16}$ and $R^{17}$, independently, are H or $CH_3$;
$R^{18}$ is selected from the group consisting of:
  a) H—,
  b) $(C_1-C_4)$alkyl,
  c) aryl$(CH_2)_m$,
  d) $ClH_2C$—,
  e) $Cl_2HC$—,
  f) $FH_2C$—,
  g) $F_2HC$—, and
  h) $(C_3-C_6)$cycloalkyl;
$R^{19}$ is selected from the group consisting of:
  a) $CH_3$,
  b) $CH_2Cl$,
  c) $CH_2CH$=$CH_2$,
  d) aryl, and
  e) $CH_2CN$;
$R^{20}$ is OH, $CH_3O$—, or F;
$R^{21}$ is:
  a) $CH_3$—,
  b) $HOCH_2$—,
  c) aniline, or
  d) $(CH_3)_2N$—$CH_2$—,
$R^{22}$ is selected from the group consisting of:
  a) HO—
  b) $CH_3O$—
  c) $H_2N$—
  d) $CH_3OC(O)O$—,
  e) $CH_3C(O)OCH_2C(O)O$—,
  f) aryl-$CH_2OCH_2C(O)O$—,
  g) $HO(CH_2)_2O$—,
  h) $CH_3OCH_2O(CH_2)_2O$—, and
  i) $CH_3OCH_2O$—;
m is 0 or 1;
n is 1–3;
p is 0–2; and
aryl is unsubstituted phenyl or phenyl unsubstituted with one of the following:
  a) F,
  b) Cl,
  c) $OCH_3$,
  d) OH,
  e) $NH_2$,
  f) $(C_1-C_4)$alkyl,
  g) $OC(O)OCH_3$, or
  h) $NO_2$;
and protected forms thereof.

14. The method of claim 13 wherein $R^1$ is selected from the group consisting of 3-fluoro-4-[4-(benzyloxycarbonyl)-1-piperazinyl]phenyl, 3-fluoro-4-(4-morpholinyl)phenyl, 4-(1,1-dioxohexahydro-1$\lambda^6$-thiopyran-4-yl)-3-fluorophenyl, 3-fluoro-4-tetrahydro-2H-thiopyran-4-ylphenyl, 3,5-difluoro-4-(4-thiomorpholinyl)phenyl, 3-fluoro-4-(3-thietanyl)phenyl, and 4-(1,1-dioxido-3-thietanyl)-3-fluorophenyl.

15. The method of claim 11 wherein $R^3$ is $C_4$–$C_7$ tertiary alkyl.

16. The method of claim 15 wherein $R^3$ is tertiary butyl.

17. The method of claim 11 wherein $R^2$ is methyl.

18. The method of claim 11 wherein X is Cl.

19. The method of claim 1 of preparing an (S)-oxazolidinone having a general structural formula:

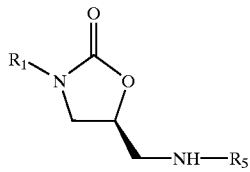

wherein $R^1$ is optionally substituted aryl, and $R^5$ is $C_1$–$C_6$ alkylcarbonyl, $C_1$–$C_6$ cycloalkylcarbonyl, $C_1$–$C_6$ alkylthiocarbonyl, or $C_1$–$C_6$ cycloalkylthiocarbonyl; or a salt or hydrate thereof, comprising:

(a) contacting a carbamate having general structural formula:

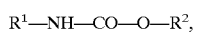

wherein $R^2$ is selected from the group consisting of $C_1$–$C_{20}$ alkyl, $C_3$–$C_7$, cycloalkyl, aryl optionally substituted with one or two $C_1$–$C_3$ alkyl or halogen groups, allyl, 3-methylallyl, 3,3-dimethylallyl, vinyl, styrylmethyl, benzyl optionally substituted on the phenyl with one or two Cl, $C_1$–$C_4$ alkyl, nitro, cyano, or trifluoromethyl groups, 9-fluorenylmethyl, trichloromethylmethyl, 2-trimethylsilylethyl, phenylethyl, 1-adamantyl, diphenylmethyl, 1,1-dimethylpropargyl, 2-furanylmethyl, isobornyl, and hydrogen;

with a (S)-protected alcohol/ester having a general structural formula:

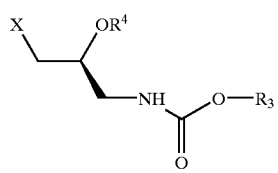

wherein X is a halogen, alkylsulfonyl, or arylsulfonyl; $R^3$ is $C_1$–$C_{10}$ alkyl; and $R^4$ is hydrogen or $C_1$–$C_5$ alkylcarbonyl;

in the presence of a lithium cation and a base whose conjugate acid has a pKa of greater than about 8, to provide an (S)-protected oxazolidinone having a general structural formula:

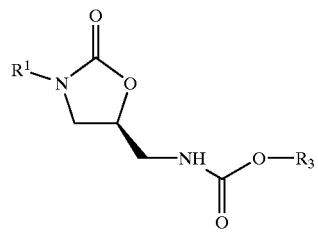

(b) contacting the reaction product of step (a) with an aqueous acid to produce an (S)-oxazolidinone free amine having a general structural formula:

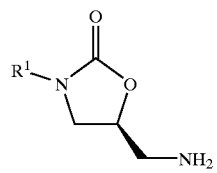

and (c) contacting the reaction product of step (b) with a base and an acylating or thioacylating agent selected from the group consisting of (i) an acid anhydride of the structural formula $O(R^5)_2$, (ii) an activated acid of the structural formula $R^5X$, or (iii) a dithioester of the structural formula $R^5S(C=S)R^5$, wherein $R^5$ is $C_1$–$C_6$ alkylcarbonyl, $C_1$–$C_6$ cycloalkylcarbonyl, $C_1$–$C_6$ alkylthiocarbonyl, or $C_1$–$C_6$ cycloalkylthiocarbonyl, and X is halogen, alkylsulfonyl, or arylsulfonyl.

20. The method of claim 19 further comprising isolating the (S)-oxazolidonone in a crystalline form.

21. The method of claim 19 wherein $R^1$ is:

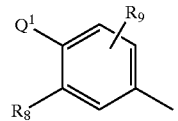

wherein $Q^1$ is: $R^{10}R^{11}N$,

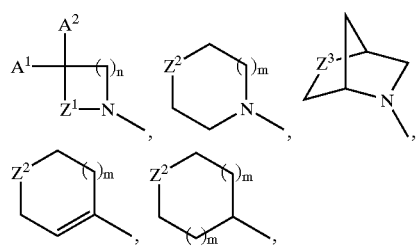

or $Q^1$ and $R^8$ taken together are dihydropyrrolidine, optionally substituted with $R^{12}$;

$Z^1$ is $CH_2(CH_2)_p$, $CH(OH)(CH_2)_p$, or $C(O)$;
$Z^2$ is $(O)_pS$, O, or $N(R^{13})$;
$Z^3$ is $(O)_pS$ or O;
$A^1$ is H or $CH_3$;
$A^2$ is selected from the group consisting of:
 a) H,
 b) HO,
 c) $CH_3$,
 d) $CH_3O$, e) $R^{14}OCH_2=C(O)NH$,
f) $R^{15}OC(O)NH$,
g) $(C_1-C_3)$alkoxycarbonyl,
h) $HOCH_2$,
i) $CH_3ONH$,
j) $CH_3C(O)$,
k) $CH_3C(O)CH_2$,
l) $CH_3C(OCH_2CH_2O)$, and
m) $CH_3C(OCH_2CH_2O)CH_2$,
or $A^1$—C—$A^2$ taken together are $CH_3$—$C(OCH_2CH_2O)$, $C(O)$, or $C(=NR^{22})$;

$R^8$ is H or F, or is taken together with $Q^1$ as above;

$R^9$ is H or F;

$R^{10}$ and $R^{11}$ are taken together with the N atom to form a 3,7-diazabicyclo[3.3.0]octane, pyrrole, pyrazole, imidazole, 1,2,3-triazole, 1,2,4-triazole, morpholine or a piperazine group, optionally substituted with $R^{13}$;

$R^{12}$ is selected from the group consisting of:
a) $CH_3C(O)$—,
b) $HC(O)$—,
c) $Cl_2CHC(O)$—,
d) $HOCH_2C(O)$—,
e) $CH_3SO_2$—,
f) $F_2CHC(O)$—,
g) $H_3CC(O)OCH_2C(O)$—,
h) $HC(O)OCH_2C(O)$—,
i) $R^{21}C(O)OCH_2C(O)$—,
j) $H_3CCHCH_2OCH_2C(O)$—,
k) benzyl$OCH_2C(O)$—,

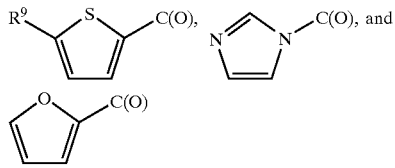

l)-m)

$R^{13}$ is selected from the group consisting of:
a) $R^{14}OC(R^{16})(R^{17})C(O)$—,
b) $R^{15}OC(O)$—,
c) $R^{18}C(O)$—,
d) $H_3CC(O)(CH_2)_2C(O)$,
e) $R^{19}SO_2$—,
f) $HOCH_2C(O)$—,
g) $R^{20}(CH_2)_2$—,
h) $R^{21}C(O)OCH_2C(O)$—,
i) $(CH_3)_2NCH_2C(O)NH$—,
j) $NCCH_2$—,
k) $F_2CHCH_2$,
l)-m)

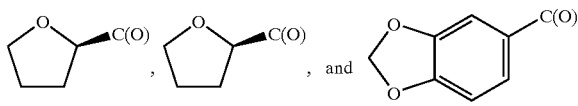

$R^{14}$ is H, $CH_3$, benzyl, or $CH_3C(O)$—;
$R^{15}$ is $(C_1-C_3)$alkyl, aryl, or benzyl;
$R^{16}$ and $R^{17}$, independently, are H or $CH_3$;

$R^{18}$ is selected from the group consisting of:
a) H—,
b) $(C_1-C_4)$alkyl,
c) aryl$(CH_2)_m$,
d) $ClH_2C$—,
e) $Cl_2HC$—,
f) $FH_2C$—,
g) $F_2HC$—, and
h) $(C_3-C_6)$cycloalkyl;

$R^{19}$ is selected from the group consisting of:
a) $CH_3$,
b) $CH_2Cl$,
c) $CH_2CH=CH_2$,
d) aryl, and
e) $CH_2CN$;

$R^{20}$ is OH, $CH_3O$—, or F;

$R^{21}$ is:
a) $CH_3$—,
b) $HOCH_2$—,
c) aniline, or
d) $(CH_3)_2N$—$CH_2$—, $R^{22}$ is selected from the group consisting of:
a) HO—
b) $CH_3O$—
c) $H_2N$—
d) $CH_3OC(O)O$—,
e) $CH_3C(O)OCH_2C(O)O$—,
f) aryl-$CH_2OCH_2C(O)O$—,
g) $HO(CH_2)_2O$—,
h) $CH_3OCH_2O(CH_2)_2O$—, and
i) $CH_3OCH_2O$—;

m is 0 or 1;

n is 1–3;

p is 0–2; and aryl is unsubstituted phenyl or phenyl unsubstituted with one of the following:
a) F,
b) Cl,
c) $OCH_3$,
d) OH,
e) $NH_2$,
f) $(C_1-C_4)$alkyl,
g) $OC(O)OCH_3$, or
h) $NO_2$;

and protected forms thereof.

22. The method of claim 21 wherein $R^1$ is selected from the group consisting of 3-fluoro-4-[4-(benzyloxycarbonyl)-1-piperazinyl]phenyl, 3-fluoro-4-(4-morpholinyl)phenyl, 4-(1,1-dioxohexahydro-1$\lambda^6$-thiopyran-4-yl)-3-fluorophenyl, 3-fluoro-4-tetrahydro-2H-thiopyran-4-ylphenyl, 3,5-difluoro-4-(4-thiomorpholinyl)phenyl, 3-fluoro-4-(3-thietanyl)phenyl, and 4-(1,1-dioxido-3-thietanyl)-3-fluorophenyl.

23. The method of claim 19 wherein $R^3$ is $C_4$–$C_7$ tertiary alkyl.

24. The method of claim 23 wherein $R^3$ is tertiary butyl.

25. The method of claim 19 wherein is $R^2$ is methyl.

26. The method of claim 19 wherein X is Cl.

* * * * *